United States Patent
Newell et al.

(10) Patent No.: US 10,760,974 B2
(45) Date of Patent: Sep. 1, 2020

(54) FLUID PROPERTY MEASUREMENT DEVICES, METHODS, AND SYSTEMS

(71) Applicant: NxStage Medical, Inc., Lawrence, MA (US)

(72) Inventors: Scott W. Newell, Ipswich, MA (US); Yakov Kogan, Bedford, MA (US)

(73) Assignee: NxStage Medical, Inc., Lawrence, MA (US)

( * ) Notice: Subject to any disclaimer, the term of this patent is extended or adjusted under 35 U.S.C. 154(b) by 252 days.

(21) Appl. No.: 15/817,183

(22) Filed: Nov. 18, 2017

(65) Prior Publication Data
US 2018/0128688 A1     May 10, 2018

Related U.S. Application Data

(62) Division of application No. 14/416,606, filed as application No. PCT/US2013/052134 on Jul. 25, 2013, now Pat. No. 9,846,085.
(Continued)

(51) Int. Cl.
*G05D 11/13* (2006.01)
*G01K 1/14* (2006.01)
(Continued)

(52) U.S. Cl.
CPC .............. *G01K 1/14* (2013.01); *G01K 7/16* (2013.01); *G01N 27/08* (2013.01); *G05D 11/135* (2013.01);
(Continued)

(58) Field of Classification Search
CPC .. G05D 11/135; G05D 11/136; G05D 11/137; G05D 11/138; G05D 11/16; G01K 2013/026
See application file for complete search history.

(56) References Cited

U.S. PATENT DOCUMENTS 3,648,523 A    3/1972   Kemper et al.
4,310,047 A    1/1982   Branson
(Continued)

FOREIGN PATENT DOCUMENTS

CN    201755338 U    3/2011
CN    202161616 U    3/2012
(Continued)

OTHER PUBLICATIONS

International Search Report and Written Opinion for International Application No. PCT/US13/52134 dated Mar. 28, 2014.

*Primary Examiner* — Kevin F Murphy
(74) *Attorney, Agent, or Firm* — Potomac Law Group, PLLC; George Dolina

(57) ABSTRACT

A system for measuring electrical conductivity includes a fluid conduction measuring circuit and a temperature measuring element having at least one thermal contact portion with a temperature sensor and a temperature measuring circuit. A controller is configured to control the conduction measuring circuit and the temperature measuring element. A fluid circuit is configured to carry a fluid and has a wetted conductor inside a conductivity cell portion, the wetted conductor having a contact, external to the fluid circuit, for interfacing with the fluid conduction measuring circuit. Further, at least one temperature measurement portion has predefined thermal properties and is configured to touch the thermal contact portion. The controller controls the temperature measuring element and the conduction measuring circuit to generate and output at least one set of contemporaneous temperature and conduction measurements.

6 Claims, 9 Drawing Sheets

Related U.S. Application Data

(60) Provisional application No. 61/675,485, filed on Jul. 25, 2012.

(51) Int. Cl.
*G01N 27/08* (2006.01)
*G05D 11/16* (2006.01)
*G01K 7/16* (2006.01)
*G01K 13/02* (2006.01)

(52) U.S. Cl.
CPC .......... *G05D 11/138* (2013.01); *G05D 11/16* (2013.01); *A61M 2205/3372* (2013.01); *G01K 2013/026* (2013.01)

(56) References Cited

U.S. PATENT DOCUMENTS

| | | | |
|---|---|---|---|
| 4,614,438 A * | 9/1986 | Kobayashi | G05D 11/16 236/12.12 |
| 4,968,151 A | 11/1990 | Thomson | |
| 5,744,027 A | 4/1998 | Connell et al. | |
| 6,677,859 B1 | 1/2004 | Bensen | |
| 6,827,487 B2 | 12/2004 | Baumbach | |
| 7,306,565 B2 | 12/2007 | Fraden et al. | |
| 7,684,446 B2 * | 3/2010 | Mcloughlin | B01F 15/0416 370/238 |
| 7,789,554 B2 | 9/2010 | Sattler et al. | |
| 7,878,703 B2 * | 2/2011 | Roberts | G05D 11/138 366/151.1 |
| 8,491,184 B2 | 7/2013 | Kamen et al. | |
| 8,764,408 B2 | 7/2014 | Smisson et al. | |
| 8,868,357 B2 | 10/2014 | Huitt et al. | |
| 2004/0007180 A1 * | 1/2004 | Yamasaki | C23C 16/16 118/715 |
| 2004/0118202 A1 | 6/2004 | Iwaki et al. | |
| 2004/0155021 A1 | 8/2004 | Norton et al. | |
| 2004/0199114 A1 | 10/2004 | Noda | |
| 2005/0065556 A1 | 3/2005 | Reghabi et al. | |
| 2007/0100666 A1 | 5/2007 | Stivoric et al. | |
| 2008/0021377 A1 | 1/2008 | Kienman et al. | |
| 2009/0012454 A1 | 1/2009 | Childers | |
| 2009/0078047 A1 | 3/2009 | Dam | |
| 2010/0009335 A1 | 1/2010 | Joseph et al. | |
| 2010/0084326 A1 | 4/2010 | Takesawa | |
| 2010/0121217 A1 | 5/2010 | Padiy et al. | |
| 2010/0269909 A1 | 10/2010 | Brandl et al. | |
| 2011/0034866 A1 | 2/2011 | Zhang et al. | |
| 2011/0274138 A1 | 11/2011 | Auret et al. | |
| 2011/0309019 A1 | 12/2011 | Ahrens | |
| 2012/0106589 A1 | 5/2012 | Ozawa | |
| 2012/0203476 A1 | 8/2012 | Dam | |
| 2012/0277673 A1 | 11/2012 | Levin et al. | |
| 2013/0257350 A1 | 10/2013 | Yen | |
| 2013/0310736 A1 | 11/2013 | Hedmann et al. | |
| 2014/0014580 A1 | 1/2014 | Ritter | |
| 2014/0116128 A1 | 5/2014 | Mantinband et al. | |
| 2014/0216560 A1 | 8/2014 | Ambrosina et al. | |

FOREIGN PATENT DOCUMENTS

| | | |
|---|---|---|
| EP | 2151673 A2 | 2/2010 |
| EP | 2366419 A1 | 9/2011 |
| JP | 2009028340 A | 2/2009 |
| JP | 2012011076 A | 1/2012 |
| JP | 2012075572 A | 4/2012 |
| WO | 2011017206 A1 | 2/2011 |
| WO | 2013133050 A1 | 9/2013 |

* cited by examiner

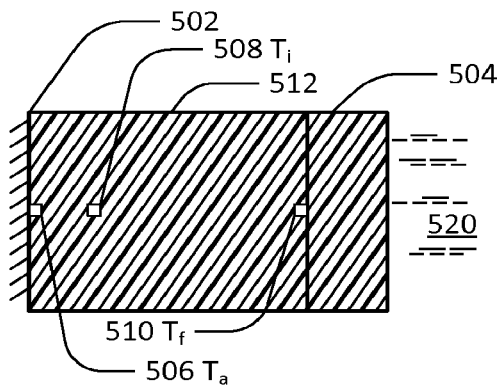
Fig. 7A
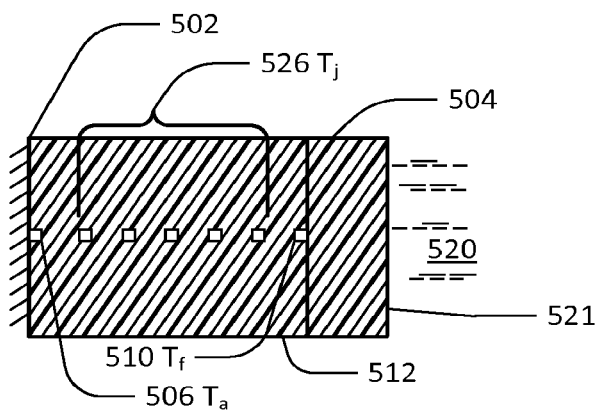
Fig. 7B
| Control error | Fluid temp indicator |
|---|---|
| Ta-Tf | Ta, Ti, or Tf |
| Ti-Tf | Ta, Ti, or Tf |
| Ta=const | Extrapolated |
| Ta=ambient | Extrapolated |
Fig. 7C

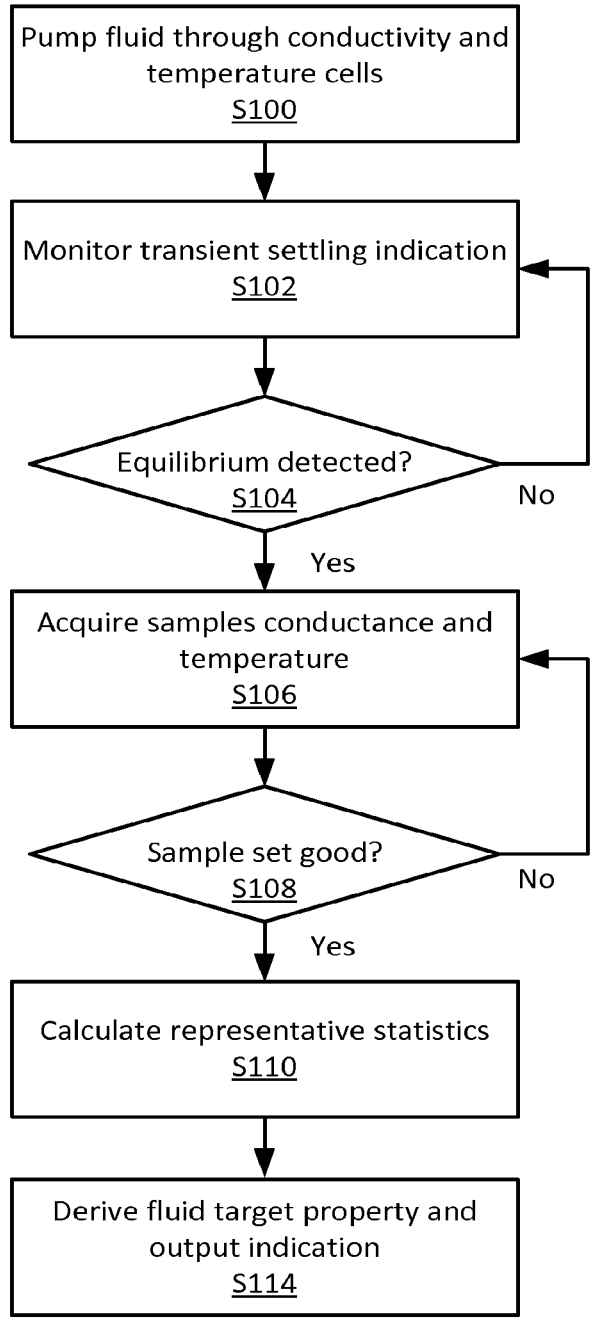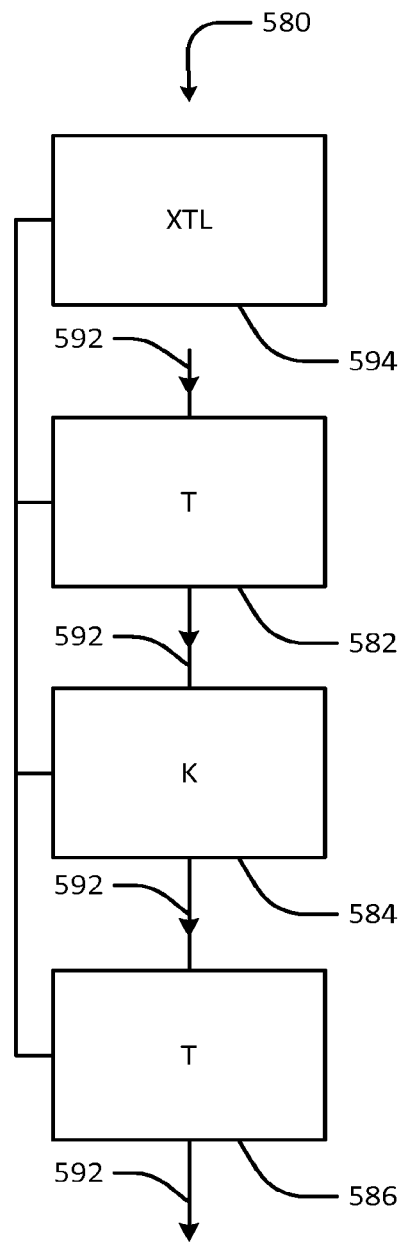
Fig. 8A
Fig. 8B

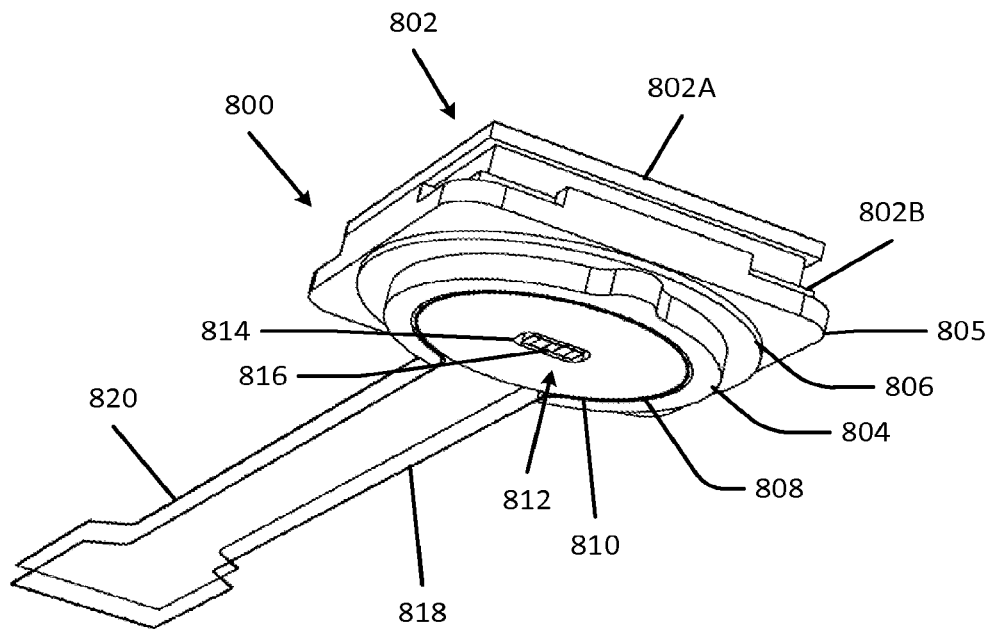
Fig. 11A
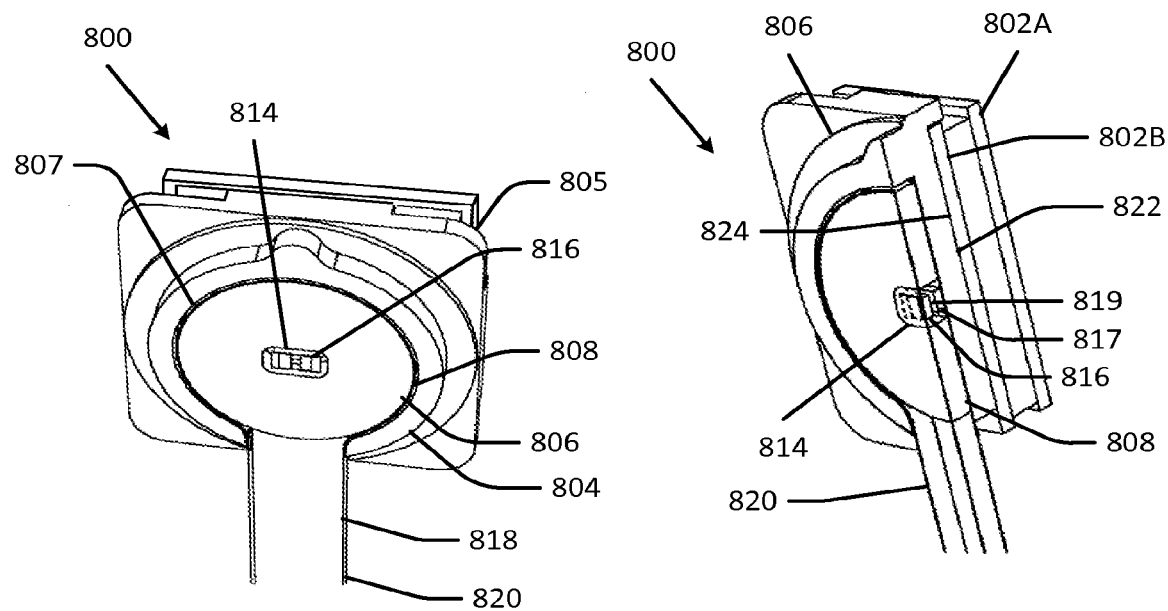
Fig. 11B
Fig. 11C

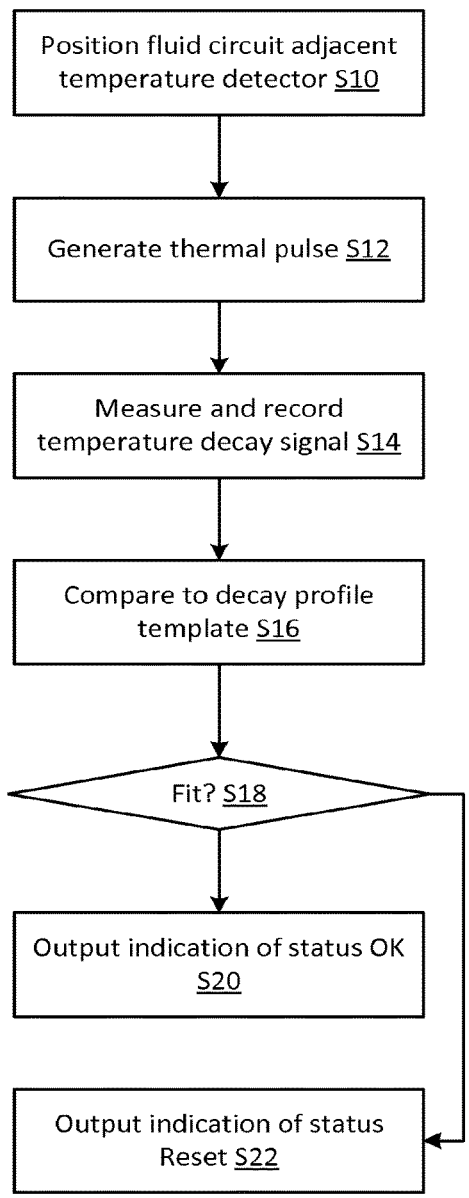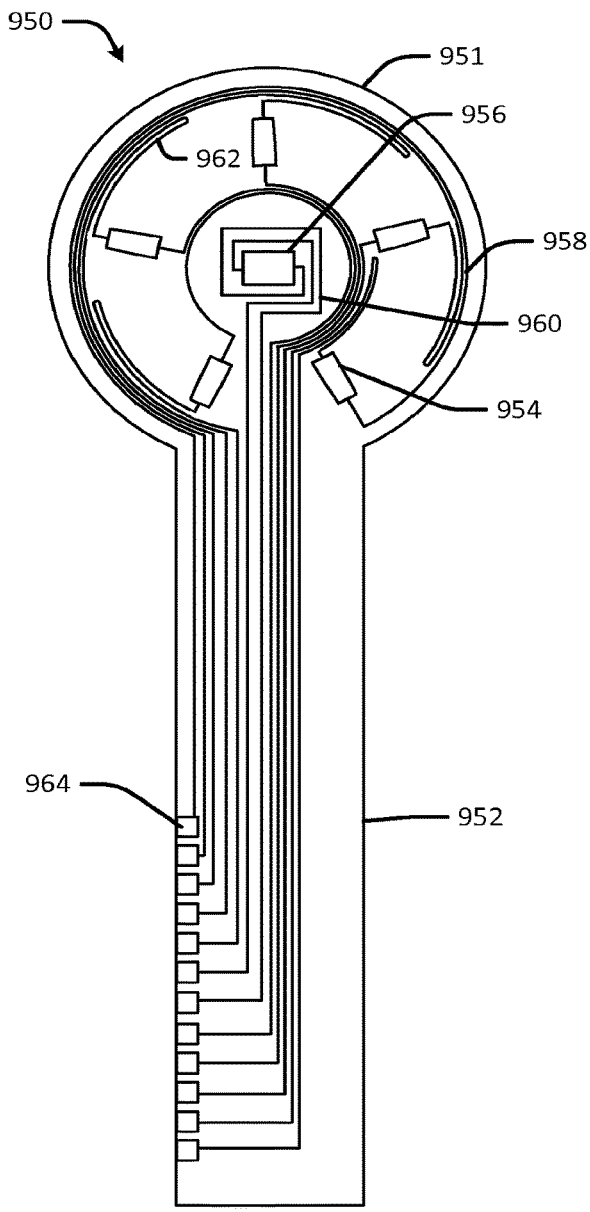
Fig. 13
Fig. 14

FLUID PROPERTY MEASUREMENT DEVICES, METHODS, AND SYSTEMS

CROSS REFERENCE TO RELATED APPLICATIONS

This application is a divisional of U.S. patent application Ser. No. 14/416,606 filed Jan. 22, 2015, which is the national stage entry of International Application No. PCT/US2013/052134 filed Jul. 25, 2013, which claims the benefit of U.S. Provisional Application No. 61/675,485 filed Jul. 25, 2012, the content of which is hereby incorporated by reference in its entirety.

BACKGROUND

The measurement of temperatures in medical devices can pose challenges. Many medical fluid flow paths are sealed and sterile, making it challenging to introduce wetted temperature sensors into the flow without risking contamination. In addition, fluid circuits for infusible fluids, medicaments, and biological fluids such as blood and plasma, are often provided in the form of disposable components, making it important for temperature measurement strategies to be compatible with low cost of such disposable components. Also, flowing blood poses a risk of forming clots when exposed to most materials and when flow paths are not smooth and conducive to non-turbulent flow, posing a challenging design constraint for sensors. Still another challenge is the need for temperature sensors in medical applications to provide high accuracy in medical applications, for diagnostic purposes, for example.

SUMMARY

High accuracy temperature measurement devices, methods, and systems for measuring the temperature of medical fluids are described. In embodiments, the devices have the features that they are compatible with the measurement of temperatures in a sealed fluid circuit, thereby promoting compatibility with sterile disposable circuits. Also described are combinations of temperature detectors, which may be active temperature detectors, and conductivity measurement for precise determination of the concentration of ions in a medicament.

BRIEF DESCRIPTION OF THE DRAWINGS

FIGS. 7A and 7B illustrate active temperature detector embodiments that employ a temperature controlled surface, which may be provided by a surface of an actively controlled heating/cooling device, according to embodiments of the disclosed subject matter.

FIG. 7C shows a table that identifies mechanisms for obtaining a fluid temperature estimate from the embodiments of FIGS. 7A and 7B, according to embodiments of the disclosed subject matter.

FIGS. 8A and 8B illustrate method and structural aspects of a conductivity measurement scheme, according to embodiments of the disclosed subject matter.

FIG. 11A shows a first view of an active temperature detector permanent part that is used for measuring temperature inside of a vessel/channel or channel, according to embodiments of the disclosed subject matter.

FIG. 11B shows further aspects of the active temperature detector permanent part of FIG. 11A, according to embodiments of the disclosed subject matter.

FIG. 11C shows further aspects, in section, of the active temperature detector permanent part of FIG. 11A, according to embodiments of the disclosed subject matter.

FIG. 13 shows a method for verifying thermal contact between an active temperature detector and a wall of a fluid vessel/channel according to embodiments of the disclosed subject matter.

FIG. 14 shows an active temperature detector with features for verifying thermal contact between a surface thereof and a wall of a fluid vessel/channel according to embodiments of the disclosed subject matter.

DETAILED DESCRIPTION OF THE DRAWINGS AND EMBODIMENTS

Figure 1:
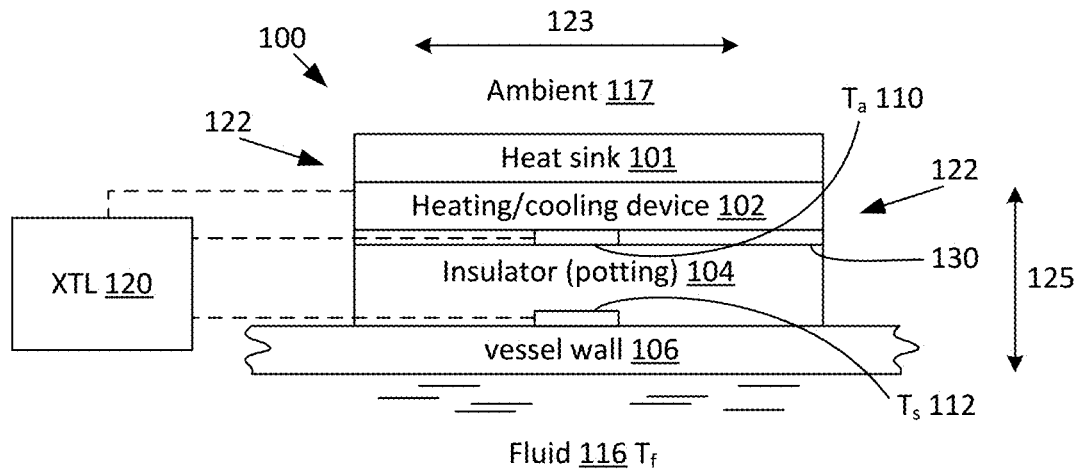
FIG. 1 is a schematic illustration of an active temperature detector and system for measuring the temperature of a fluid in a vessel/channel or channel, according to embodiments of the disclosed subject matter.

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

The disclosed subject matter provides a mechanism, device, system, and method for accurately measuring a fluid temperature inside a vessel. The term vessel/channel for purposes of the invention may encompass any fluid containing device including one that conveys fluid in a continuous or intermittent flow, or storage container. Fluid vessels may include containers and fluid conveyances such as flexible wall bags, panel-type flow through channels, or tubes. According to embodiments, the disclosed subject matter may be used for measuring the temperature of fluid contained by a vessel/channel having a wall having any properties, but finds particularly merit in applications where the wall presents a substantial thermal resistance between the fluid and the temperature sensor, such as when a temperature sensor is located outside the vessel/channel wall.

A feature of the disclosed devices and methods is the substantial negation of heat flow between the fluid and the sensor that can otherwise occur due to any difference in temperature between the ambient environment outside the vessel/channel and the fluid. Active temperature compensation according to the disclosed embodiments may improve the fluid temperature sensing accuracy and may also reduce the measurement response time.

In embodiments of the disclosed subject matter, one or more temperature sensors such as thermistors, thermocouples, RTD, quartz thermometers, etc., are placed against a surface of a fluid vessel/channel or channel such that the temperature sensor is separated by a wall of the fluid vessel. To illustrate the operation of the active temperature detector, the operation of this configuration is now discussed in the absence of active temperature compensation.

A side of the temperature sensor opposite the vessel/channel wall is adjacent an external environment which is, at least at certain times, at a different temperature from that of the fluid so that heat is conducted from, or to, the fluid and the external environment. The wall and the path to the external environment represent thermal resistance to heat flow through the vessel/channel wall. The thermal resistance can be substantial for vessels with low conductivity such as plastic vessels. The resistance in the heat flow places the temperature sensor at a temperature intermediate between that of the fluid and that of the external environment.

The thermal properties of the vessel/channel wall can also result in undesirable transient effects. The thermal properties of the wall include thermal capacitance as well as conductivity and the ratio of the wall's conductivity to capacitance, i.e., the thermal diffusivity, determines the responsiveness, or settling time, of the fluid-side temperature sensor measurement. Long settling times can lead to inaccurate temperature indications when the fluid temperature changes rapidly.

For such a passive temperature sensor configuration, the error in temperature indication of an uncompensated sensor can be calculated as follows. If $R_a$=Thermal resistance between sensor and ambient; $R_w$=Thermal resistance between sensor and fluid through the vessel/channel wall (bag); $T_f$ is the fluid temperature and $T_a$ is the ambient temperature, then the sensor temperature error $T_e$ at equilibrium will be $$T_e=(T_f-T_a)*[R_f/(R_f+R_a)].$$

This calculation is simplified and assumes the system can be modeled as a simple thermal network. The inherent approximations relative to the real world should be evident from the foregoing discussion. In addition, the transient response of the system which is not described in further detail is more complex, but is also addressed by active temperature detectors according to the disclosed embodiments.

The disclosed subject matter includes embodiments of an active sensor device that combines a fluid-side temperature sensor with a heating/cooling device (for example, a thermoelectric device) and a heat flow sensor. In all of the embodiments, a heating/cooling device (meaning a heating or cooling device or one capable of heating or cooling) is incorporated in apparatus defining a thermal network that includes at least one temperature sensor and preferably two. The device is placed in thermal contact with the wall of a vessel/channel or channel containing a fluid whose temperature is to be measured. The thermal network is any kind of components that can transfer heat between the wall and the heating/cooling device and which network can be allow a controller to calculate the fluid temperature from the indicated temperature of the at least one temperature sensor and/or regulate the heating/cooling device so as to halt any thermal gradient in the thermal network such that the temperature of the at least one temperature sensor must be equal, in the steady state, to the fluid temperature. In embodiments where two temperature sensors are used, one may be distinguished from the other by being closer to the fluid and the other closer to the heating/cooling device.

Referring to FIG. 1, an active temperature detector 100 has a fluid-side temperature sensor 112 positioned adjacent the wall 106 of a vessel. A heating/cooling device 102 is positioned on a side of the fluid-side temperature sensor 112 opposite the fluid vessel/channel wall. Note that in the present disclosure, in any of the embodiments in a wall separating the active temperature detector and the fluid may be that of a vessel, container, a flow path, a fluid circuit element or any other fluid containing or carrying device. The heating/cooling device 102 generates heating or cooling effect that is regulated to maintain a temperature of the fluid-side temperature sensor 112, on a side opposite the vessel/channel wall, at substantially the same temperature as that of the fluid such that there is, substantially, no heat flow through the vessel/channel wall 106. To provide the control of the heating/cooling device 102, the active sensor device further includes a control component that generates a control signal that indicates a temperature difference to be minimized or a thermal flux measurement.

The control component, in the present embodiment, includes a heating/cooling side temperature sensor 110 and a controller 120, which may have a user interface for receiving commands and outputting data. The heating/cooling side temperature sensor 110 is separated from the fluid-side temperature sensor 112 by a material that provides a thermal resistance, in the example an insulator 104 that may be formed from potting material (e.g., epoxy, thermoplastic, laminated glass epoxy) that supports the components and forms an integrated device with uniform thermal contact between components. In the present embodiment, the controller 120 receives signals from the fluid-side temperature sensor 112 and the heating/cooling side temperature sensor and generates an error signal responsively to them, for example, the error signal may be a difference between the temperature indications of the fluid and heating/cooling side temperature sensors 112 and 110. The controller 120 uses the error signal to regulate the heating/cooling device so as to minimize the difference between the temperature indications of the heating/cooling side temperature sensor 110 and the fluid-side temperature sensor 112. For a physically wide active temperature detector (width being indicated by arrows 123 and the direction normal to the page), heat flow is substantially entirely limited to flow in the direction joining the fluid and heating/cooling side temperature sensors. Thus, the above-described error signal is effectively an indication of all heat flow through the vessel/channel wall 106. Because this heat flow is negated by the control of the heating/cooling device 102, then the fluid and heating/ cooling side temperature sensors 112 and 110 will both indicate the fluid temperature. The fluid temperature signal indicated by the device 100 may be taken from the fluid and heating/cooling side temperature sensors 112 and 110 or an average of both.

In the embodiment 100, the thermal resistance of the insulator 104 may be selected to be comparable to that of the vessel/channel wall, higher, or lower. For temperature measurements where slow transient response is acceptable, a material with a low conductivity, with a concomitantly low thermal diffusivity, will provide an error signal (based on the indicated temperature difference of the ambient-side and fluid-side temperature sensors 110 and 112) whose magnitude is greater for a given heat flux. This may improve temperature measurement precision. For temperature measurements where faster transient response is required, a material with a higher conductivity and a concomitantly high thermal diffusivity, will provide a smaller error signal for a given heat flux, but will provide shorter settling time and thereby "follow" a variable fluid temperature more accurately.

The thermoelectric device generates a heat or cooling effect at a rate controlled to maintain a surface such that surface of the thermoelectric device that faces the sensor is controlled such that its temperature is equal to the fluid temperature. In this case $T_a = T_f = T_s$ and the measurement error approaches zero. For cooling effect, an active heat pump may be used, for example a thermoelectric heat pump may be used. For measurement of temperatures that are above ambient, the heating/cooling device may be a heater that provides cooling effect by means of heat transfer to the surrounding environment.

To enhance the heat transfer from the insulator 104, vessel/channel wall 106, and temperature sensors 110 and 112, a heat sink may be employed on the heating/cooling device 102. In a heating/cooling device that is simply a dissipative heater (such as an electrical resistance heater), the heat sink may provide passive cooling through the dissipative heater to the ambient environment. Thus, for effective transient operation, heat stored in the insulator 104 and other components may be rejected to allow for equilibration of the temperature sensors when a negative-going change in fluid temperature occurs. This may be provided by ensuring that the electrically dissipative heater transfers heat effectively to the heat sink 101. An active heating/cooling device such as a thermopile will employ a heat sink of some type but may actively pump heat to/from the heat sink and the insulator 104 and other components. For most applications it may be desirable to employ an electrically dissipative heater (resistive or semiconductor) or thermoelectric device for the heating cooling device 102, however, the heating cooling device 102 (including heat sink 101) may be replaced with an active heating cooling device employing a mechanical system such as a container whose internal temperature is thermostatically regulated.

In embodiments, the controller 120 may include a feedback control circuit that regulates current to the heating/ cooling device 102, which may be, for example, a thermoelectric heat pump (e.g., thermopile) or dissipative heater. The current may be supplied and controlled using linear or switching power technology. The controller 120 regulates the temperature of the heating/cooling device 102 so that the temperature indicated by the heating/cooling side temperature sensor 110 is equal to, or transiently approaches, the temperature indicated by the fluid-side temperature sensor 112. When these two temperatures are equal, there is no net heat flow between them. Because effectively all heat that flows between the two sensors also flows between the fluid-side temperature sensor 112 and the heating/cooling side temperature sensor 110.

According to the foregoing embodiments, a temperature sensing error that results due to heat flowing from a fluid to the ambient environment through the vessel/channel wall 106 is minimized. The heat flow through the vessel/channel wall 106 is primarily normal through the wall, but some heat flow through the ends 122 of the insulator 104 occurs. The isothermal environment is provided for the fluid-side temperature sensor 112 using active control as described. The heating/cooling device 102 may have a surface 130 of a low thermal resistance material such as Aluminum Nitride ceramic to ensure a uniform temperature of the surface interfacing the insulator 104 is provided. The size of the sensor surface 130 may be made much larger than the size of the sensor 112 and the thickness of the insulator 104 may be made low such that the temperature of the insulation 104 and vessel/channel wall 106 near the sensor 112 to reduce thermal storage in the insulator 104 and decrease heat transfer from the ends 122 and thereby maintain the temperature of the fluid-side temperature sensor very close to the temperature of the heating/cooling device 102 surface 130.

A heat sink 101 may or may not be provided depending on the properties of the system and/or the type of thermoelectric device. For example, in an embodiment with a low aspect ratio and high heat flow from the ends 130 may not require a separate heat sink 101. The control system parameters may be chosen to allow the temperature indicated by fluid-side temperature sensor 112 to track closely the temperature of the target fluid 116. In embodiments, the controller 102 may employ proportional-integral-derivative controller (PID controller) or feed-forward control features. A feed-forward controller may employ an internal model and fit two or more spaced temperature measurements within the insulator 104 to a predictor of the fluid temperature to more rapidly adjust the heating/cooling device 102 temperature.

The active sensor device 100 reduces the response time of the thermal measurement. The relatively high heat flow provided by the heating/cooling device in combination with a high controller gain may provide higher thermal gradients in the sensor, as compared to a passive sensor, which drive the sensor temperature to settle to its final value faster.

Some details of background technology for temperature sensors are described in U.S. Pat. Nos. 3,933,045 and 4,968,151, which are incorporated by reference in their entireties herein.

In alternative embodiments, the device that generates an indication of heat flux may include a heating/cooling side temperature sensor separated from the fluid-side temperature sensor with a material between them that provides thermal resistance as described with reference to FIG. 1. Alternative embodiments may employ a separate heat flux sensor. For example, a heat flux sensor may be attached to the ambient-facing side of the fluid-side temperature sensor 112, taking the place of the insulator and heating/cooling side temperature sensor. In yet another alternative embodiment, a flux sensor may be combined with the active temperature detector device 100 of FIG. 1 and located at an intermediate position within the insulator 104. As mentioned, in still other embodiments, temperature sensors may be located at multiple positions within the insulator 104 and used to estimate of net heat flow through the vessel/channel wall 106 which is then used as the control input for the controller. In embodiments, the multiple temperature indications may be combined to reduce random error or combined and used for feed-forward control as mentioned.

Figure 2:
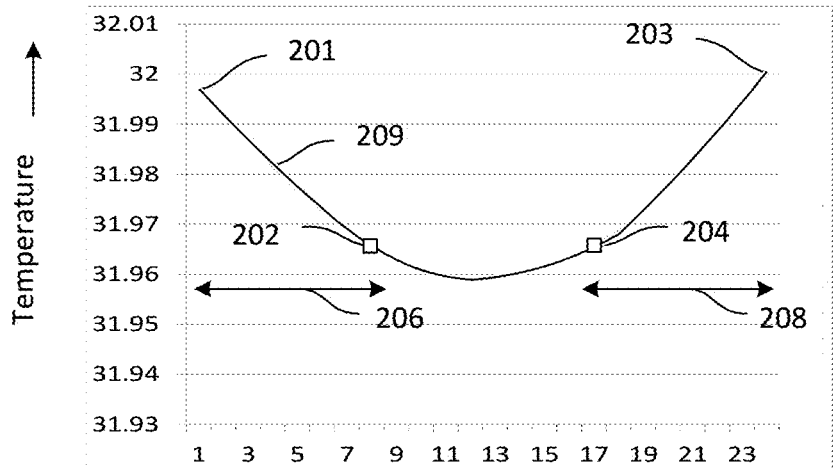
FIG. 2 shows a temperature distribution in a solid containing temperature sensors for discussion of features of the disclosed subject matter.

In a particular alternative embodiment, in contrast to embodiment 100 where the heating/cooling side temperature sensor 110 is located directly adjacent the heating/cooling device 102, a heating/cooling side temperature sensor may be positioned intermediate between the heating/cooling device 102 and the fluid-side temperature sensor 112. For example, a heating/cooling side temperature sensor may be separated from the heating/cooling device 102 by an ambient-side insulator that has the same or similar dimensions and thermal properties as that of the vessel/channel wall 106. In FIG. 2, a curve 209 indicates a temperature profile between the heating/cooling device at 201 and the fluid at 203. The vessel/channel wall spans the gap 208 and the ambient-side insulator spans the gap 206. The arched temperature profile arises due to a small heat flow from the ends (indicated at 122) of the active temperature detector 100 as modified according the present embodiment. The temperature indicated by the fluid-side temperature sensor is shown at 204 and the temperature indicated by the heating/cooling side temperature sensor is shown at 202. Because of the symmetrical arrangement, the minimization of the difference between the fluid and ambient side temperature indications 202 and 204 drives the temperature of the heating/cooling device interface 201 toward the fluid temperature 203.

In any of the disclosed embodiments, the temperature sensor closest to the fluid vessel/channel may be separated therefrom by additional elements such as adhesive, thermal paste, or structural members. The disclosed embodiments may be applied to applications for the measurement of temperatures of fluids and other materials including solids, gas, liquid, and multiphase fluids.

A pump 133 that regulates a rate of flow of fluid 116 through a fluid circuit partly enclosed by the wall 106. The fluid circuit may be any type of fluid circuit. The circuit may have flat portions such as expanded elements of a circuit defined between parallel panels that are molded or seam welded to define flow paths between them. The controller 120 may be configured to activate the heating/cooling device 102 only when a flow of a predefined magnitude is established so as to avoid the risk of causing heat buildup in the fluid 116 or erroneous temperature measurements. The predefined flow may be established by regulation of the pump 133. In an embodiment, the controller 120 only permits the heating/cooling device 102 to activate, and temperature samples to be acquired, when the pump is operated at a predefined minimum speed.

Figure 3:
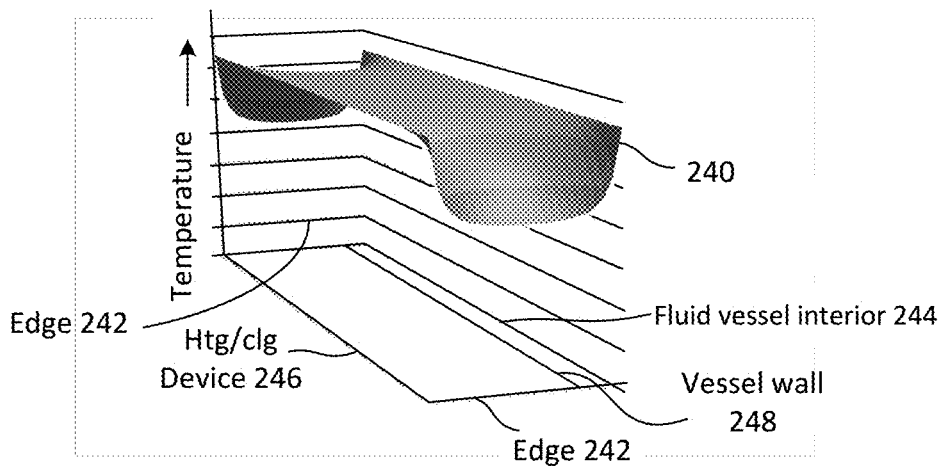
FIG. 3 is a three-dimension view of a temperature profile along two axes for discussion of features of the disclosed subject matter.
Figure 4:
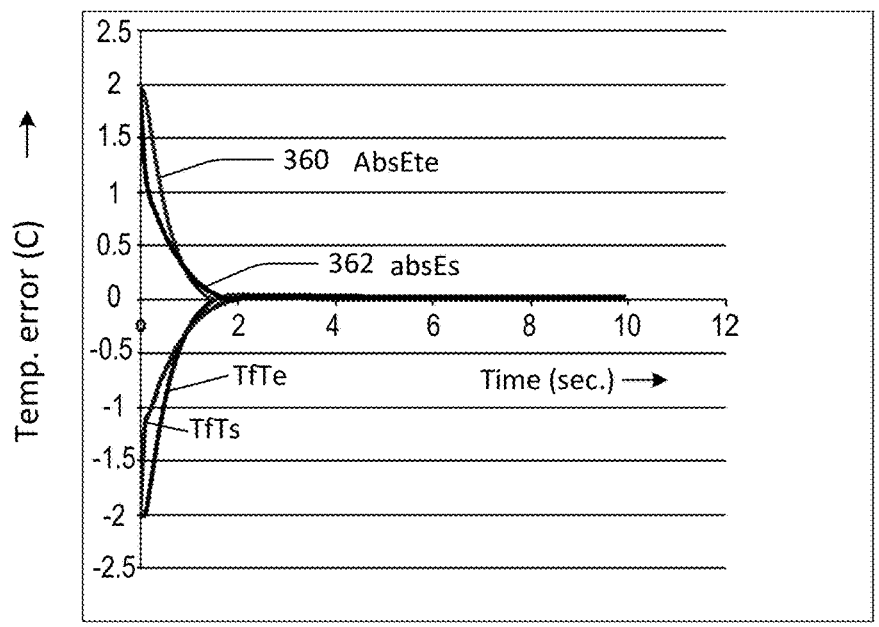
FIG. 4 shows a time profile of temperature error for a control scenario embodiment where the difference between two temperature sensors in a symmetrical arrangement is used as the control input, according to embodiments of the disclosed subject matter.

Referring now also to FIG. 3, a surface plot 240 shows the temperature distribution at steady state including the vessel/channel wall 106 (edge 244 coinciding with the fluid) and the insulator 104 with the fluid 116 and heating/cooling device 102 (boundary of heating/cooling device 102 is indicated at 246) providing boundary conditions as well as edges 242. The plot shows the temperature distribution for a device with an aspect ratio of 4.5 (width 123 to thickness 125). The insulator simulated had the same properties as the fluid vessel/channel wall and it was assumed there was not separate contact resistance at the interface of the vessel/channel wall with the insulator. It may be seen that despite the low aspect ratio of 4.5, the temperature profile along the middle shown in FIG. 2 only deviates by 0.3% of the temperature difference between the fluid 32C and the ambient 20C. Also, when the temperature of the heating/cooling device interface 201 is used as the indicator of fluid temperature, the deviation is lower. FIG. 4 shows a time profile of temperature error for the control scenario discussed above where the difference between the two temperature sensors in the symmetrical arrangement discussed with reference to FIG. 2 is used as the control input. That is, the controller minimizes the difference between the fluid and ambient side temperature indications 202 and 204, to drive the temperature of the heating/cooling device interface 201 toward the fluid temperature 203. The reference numeral 360 indicates the absolute value of the difference between sensors at 202 and 204 as described with reference to FIG. 2. It can be seen with simple proportional control that the system settles to near zero error within 2 seconds after an instantaneous fluid temperature change of 2C. For this simulation, it was assumed that the heater response was immediate with a simple proportional control.

Figure 5:
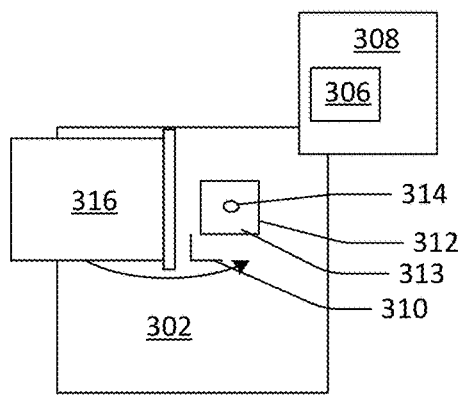
FIG. 5 illustrates a device with an integrated temperature sensor that includes an active temperature detector according to any of the embodiments of the disclosed subject matter.

FIG. 5 illustrates a device 302 with an integrated temperature sensor that includes an active temperature detector device 312 according to any selected one of the foregoing embodiments. The active temperature detector device 312 has a contact temperature sensor 314 with a surface configured to make thermal contact with a vessel/channel 306 integrated in an installable component 308 which is attached by way of an attachment mechanism 310 to the device 302. The vessel/channel 306 may be a panel shaped fluid circuit component or a flexible-walled container and the component 308 may be a fluid circuit, for example, one installable on a medical treatment device. The device 302 may be a medical treatment device, for example, a dialyzer. The active sensor device 312 further includes a contact portion 313 that provides the same heat transfer properties as the contact temperature sensor 314. A heating cooling device and an ambient side temperature sensor (not shown) as well as other elements behind the contact temperature sensor 314 and contact portion 313 operate as described above to measure the temperature inside the vessel/channel 306. A movable component 316 may be closed over the component 308 and configured to hold the vessel/channel 306 against the combined surface of the temperature sensor 314 and contact portion 313. In embodiments, the active temperature detector device may be integrated in a bag support in which the weight of fluid in the bag holds the wall of the bag against the temperature detector 314 and contact portion 313 or in which pumping pressure is used. The device 302 may include controller components.

Figure 6:
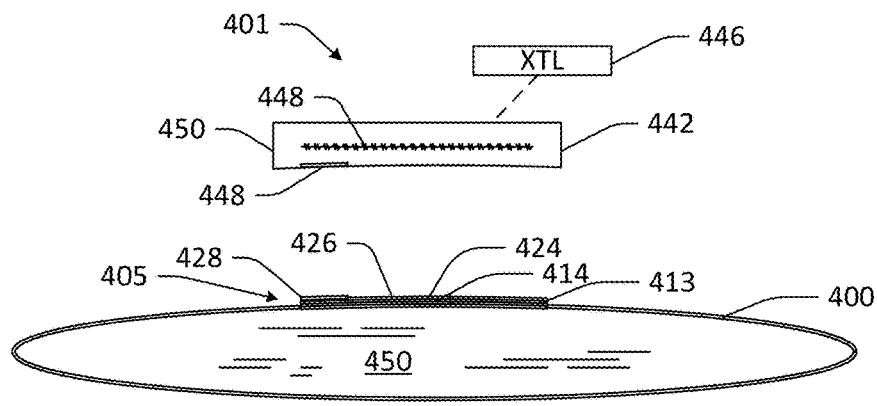
FIG. 6 shows a disposable active temperature detector, according to embodiments of the disclosed subject matter.

FIG. 6 is a disposable version of an active temperature detector. FIG. 6 illustrates a fluid vessel/channel 450 with a temperature measurement component 405 and a complementary measurement device 401. The temperature measurement component 405 may incorporate a series of layered components including a fluid-side temperature sensor 414 and a heating/cooling side temperature sensor 424 separated by a thermally insulting film 413. In an alternative embodiment, the heating/cooling side temperature sensor is included in component 450 and not a part of the temperature measurement component 405. An electrically dissipative heater 426 may be attached to the above opposite a wall 400 of a fluid container 450. An insulating layer may be positioned between the electrically dissipative heater 426 and the heating/cooling side temperature sensor 424 to provide a symmetric arrangement as discussed above with reference to FIG. 2. Electrical contacts 428 may be connected to the sensors 414 and 424 and to the current leads of the electrically dissipative heater 426 and arranged to mate with complementary connectors 448 on the complementary measurement device 401. A controller 446 and interface component 442 may be provided as part of the complementary measurement device 401 and forming a permanent fixture. The temperature measurement component 405 and container 450 may be configured as a disposable component, for example a flexible walled bag with the temperature measurement component being a laminated structure that is thermally welded or adhesively bonded thereto. In an alternative embodiment, an electrically dissipative heater 448 is incorporated in the permanent complementary measurement device. In this embodiment, the contacts 428 and 448 would not include current contacts for a heater integrated in temperature measurement component 405.

Referring now to FIGS. 7A and 7B, in alternative embodiments, an active temperature detector employs a temperature controlled surface 502, which may be provided by a surface of an actively controlled heating/cooling device such as described with reference to the foregoing embodiments. A container wall 504 separates a fluid 520 from a temperature sensor 510. Temperature sensor 510 and additional sensors 506 and 508 within an insulating body 512 (which may be formed of one or more layers that are not shown). In another embodiment, multiple sensors 526 lie within the insulating body 512.

Referring to FIG. 7C, a table 550 identifies four mechanisms (552, 554, 556, and 558) for obtaining a fluid temperature estimate from the embodiments of FIGS. 7A and 7B. The first column 560 identifies the error signal for feedback control of the temperature of the temperature controlled surface 502. The second column 562 identifies the indicator of the fluid temperature, which is the temperature of the fluid 520 whose magnitude is indirectly measured by the embodiments.

In embodiment 552, the error signal is the difference between a temperature of the temperature controlled surface 502, or a temperature of the insulator 512 close to the temperature controlled surface 502 (indicated at 506), and a temperature of the vessel/channel wall 504, or a temperature of the insulator 512 close to the vessel/channel wall 504 (indicated at 510). In any case, 506 indicates a temperature sensor that indicates substantially the temperature $T_a$ of the temperature controlled surface 502 and 510 indicates a temperature sensor that indicates substantially the temperature $T_f$ of the vessel/channel wall 520. The difference $T_f$-$T_a$ is applied as an input to the controller to raise or lower the temperature of the temperature controlled surface 502. In the present or any of the embodiments, the controller (not shown in the present figures but as described earlier) may employ any appropriate control algorithm or apparatus, for example, a proportional, integral, differential control scheme, proportional differential control scheme, proportional, integral; integral; or simple proportional control scheme. Another simple alternative is simple limit cycle control such as used in thermostats. The controller also may employ open loop control using the error or the individual inputs themselves to predict the temperature error and regulate $T_a$ accordingly. In embodiment 552, the output indicating fluid temperature may be $T_a$, $T_f$ or some temperature $T_i$ at indicated by a sensor 508 located at an intermediate point in the insulator 512. Note that variations of the embodiment 552 can be formed by using intermediate temperatures such as Ti as part of the error signal (e.g., $T_a$-$T_i$, $T_s$-$T_f$ or two intermediate temperatures) where any two intermediate temperature sensors at different locations in the insulator are used to indicate a heat flow between the surface 502 and the fluid.

Embodiment 554 is an example where an error $T_f$-$T_i$ is used for control of the temperature controlled surface 502, $T_f$ and $T_i$ are indicated by the intermediate sensor 508 and sensor 510 and in which sensor 508 is positioned so that the thermal resistance between it and the temperature controlled surface 502 is substantially the same as the resistance between sensor 510 and the fluid 520. In embodiment 554, the output indicating fluid temperature may be $T_a$, $T_f$ or $T_i$.

In embodiment 556, multiple temperature sensors 526 located in the insulator 512 indicate temperatures $T_j$ at various positions in the insulator 512, thus indicating a temperature profile therewithin. In this embodiment, the temperature controlled surface 502 may be regulated to hold a constant temperature. As the temperature of the fluid 520 changes, temperature disturbances pass through the vessel/channel wall 504 and into the insulator 512 changing the temperature profile indicated by temperatures $T_j$. A controller may employ a processor to form a curve to the temperature profile $T_j$ and then use a point extrapolated therefrom as an indication of the fluid temperature. In other words, the temperature profile at any given time is given by the fitted curve and includes, by extrapolation, the temperature of the interior surface 521 of the vessel/channel wall 520. This computed temperature may be output by the controller as the fluid temperature. In a variation, indicated by embodiment 558, employs an internal model of the thermal system including the insulator 512, the vessel/channel wall 504, and if desired, other features such as the film coefficient at the surface 521. In this embodiment, the model is fitted to the measured data points $T_j$ and the fluid temperature estimated from the model's representation of the fluid temperature.

Although in the foregoing embodiments, a member lying between the vessel/channel wall and the heating/cooling device (or schematically, the temperature controlled surface 502) is identified as an insulator, this is not intended to indicate a limited range of materials. Materials with any suitable combination of thermal capacitance and conductivity will possess some degree of resistance to heat flow and thereby fall within the term insulator. In addition, the insulator may or may not include multiple layers or otherwise form a composite structure. The insulator may incorporate cooling features such as layers of high conductivity material to promote the transfer of heat in specific directions, for example. In specific embodiments it may be desirable to choose an insulator material or materials whose thermal properties are close to those of the vessel/channel wall.

Other variations of the foregoing embodiments include ones in which instead of a vessel/channel wall lying between the active temperature detector and a target substance, some other thermal resistance is present, for example, a material overlying a solid body whose temperature is desired to be measured. Also, as mentioned above, instead of additional temperature sensors being embedded in an insulator, a separate thermal flux transducer may be employed.

Referring now to FIGS. 8A and 8B, a conductivity measurement device 580 has a continuous flow path 592 leading to a first temperature measurement cell 582, then to a conductivity measurement cell 584, and then to a second temperature measurement cell 586. The first and second temperature measurement cells provide temperature measurement readings of the fluid temperature flowing through the continuous flow path 592. The temperature reading provided by the first measurement cell 582 may be combined with those from the second measurement cell to generate a statistic representing the temperature of the fluid at the point where its conductivity is measured by the conductivity measurement cell. For example, the two temperature measurements may be averaged over a time interval during which the fluid flows at a constant rate. During this time interval, the conductivity of the fluid flowing through the conductivity cell may be measured using a wetted electrode resistance measurement through a fixed length of the flow path. The process takes place while a continuous flow exists in the flow path 592. A controller 594 may receive the temperature and conductivity measurements and detect the conditions for sampling and storing measurement data, deriving a statistic therefrom, and calculating the fluid properties from the statistic. A single temperature sensor may be used as well. The single sensor embodiments, may advantageously locate the single sensor close to the fluid. Any of the embodiments may be modified to use a single temperature sensor. In all of these, the temperature sensor may be located adjacent to, or close to the fluid.

The above measurement process using the system 580 is now described with reference to FIG. 8A. Fluid is pumped through the conductivity and measurement cells at S100. While the fluid is flowing, one or more transient variables are monitored until an equilibrium condition is established. The equilibrium condition may coincide with, for example, an unchanging temperature, an unchanging raw conduction measurement indication, an unchanging flow rate, or with an unchanging flux measurement for the active temperature detector device described above, if used for temperature measurement. Once the equilibrium condition is detected at S104, samples of conductivity and temperature are obtained and stored at S106. The sample data may be tested against predefined limits to ensure the sampled data are valid and if they pass, at S108, representative statistics may be derived at S110. Fluid parameters such as salinity, concentration, species molarity, or other parameters of interest may be generated by correlation of the raw conduction or conductivity measurement and temperature statistic with the parameter of interest at S114. The fluid temperature is measured to compensate the conductivity measurement to allow for accurate determination of a fluid property, such as ion concentration or standardized conductivity (e.g., referred to a standard temperature such as 25C). This may be done internally by a controller and operations of a fluid handling device may be automatically governed by the outcome. For example, a fluid handling system may alert an operator to an improper fluid property determination or it may shut down an operation such as a treatment showing an improper concentration of a medicament. A variety of different operating regimes may be responsive to an output of the property measurement and determination disclosed herein.

Figure 9A:
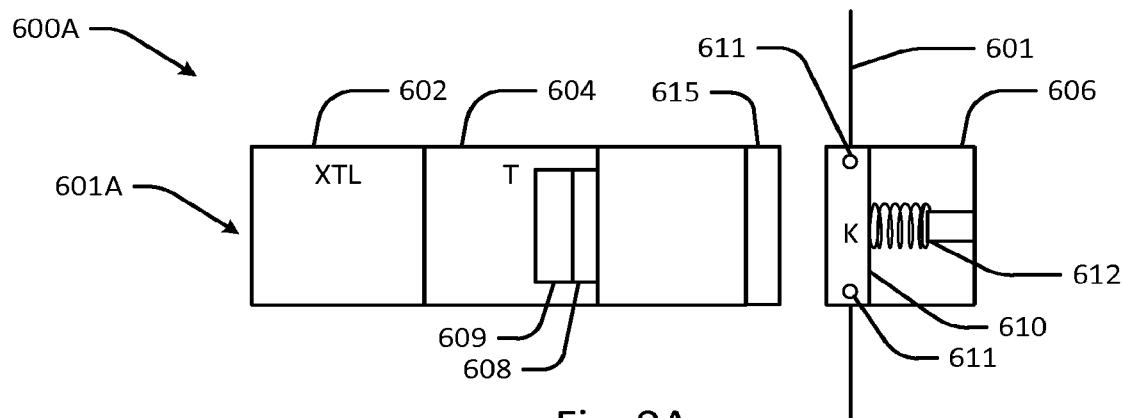
FIG. 9A shows a conductivity measurement device with a controller, an active temperature detector and a conductivity/temperature measurement cell in a module which may form a disposable component, in a first configuration prior to use, according to embodiments of the disclosed subject matter.

Referring now to FIG. 9A, a conductivity measurement device 600A has a controller 602, an active temperature detector 604 (together forming a measurement component 601A) and a conductivity/temperature measurement cell 610 in a module 606 (which may form a disposable component). A fluid line 601 carries fluid into the conductivity/temperature measurement cell 610. A pair of conductors 611 in the cell connected to a driver circuit (current source and voltage measurement circuits) in the controller to measure the fluid conductance in the fluid column between the conductors 611. An insulator 608 with temperature sensors, a heating/cooling device 609, and the controller 602 may be configured as described according to any of the embodiments described herein to measure the temperature of fluid in the conductivity/temperature measurement cell 610. The module 606 has an urging mechanism 612 that urges the conductivity/temperature measurement cell 610 against the insulator 608 to ensure good and uniform contact between the planar area of the conductivity/temperature measurement cell 610 and the insulator 608. At the same time, the urging mechanism may also mate, and ensure good electrical contact, between electrical contacts that connect the conductors 611 to contacts of a driver circuit within the controller 602. A support aligns and supports the module 606 and provides a base for urging mechanism 612. FIG. 9A shows the permanent component 601A prior to connection to the measurement component 601A and FIG. 9B after connection.

Figure 9B:
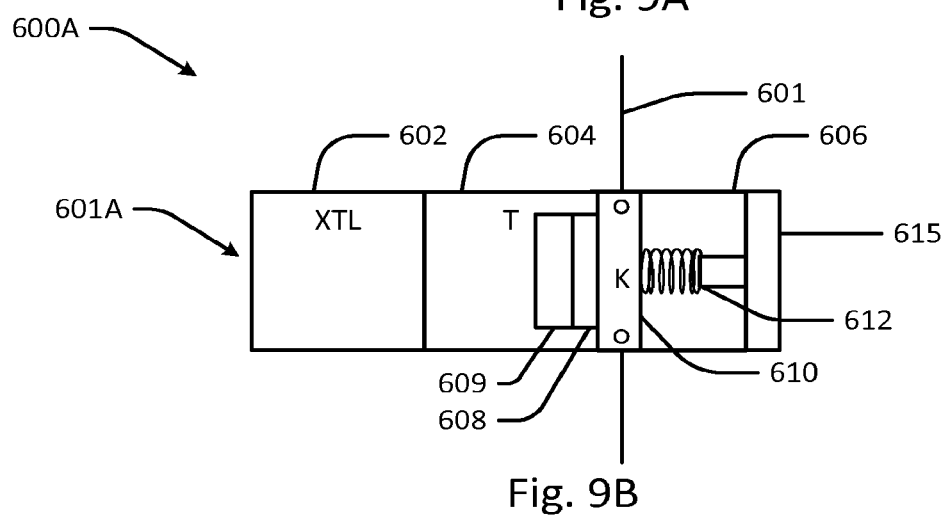
FIG. 9B shows a conductivity measurement device with a controller, an active temperature detector and a conductivity/temperature measurement cell in a module which may form a disposable component, in a second configuration adapted for use, according to embodiments of the disclosed subject matter.
Figure 9C:
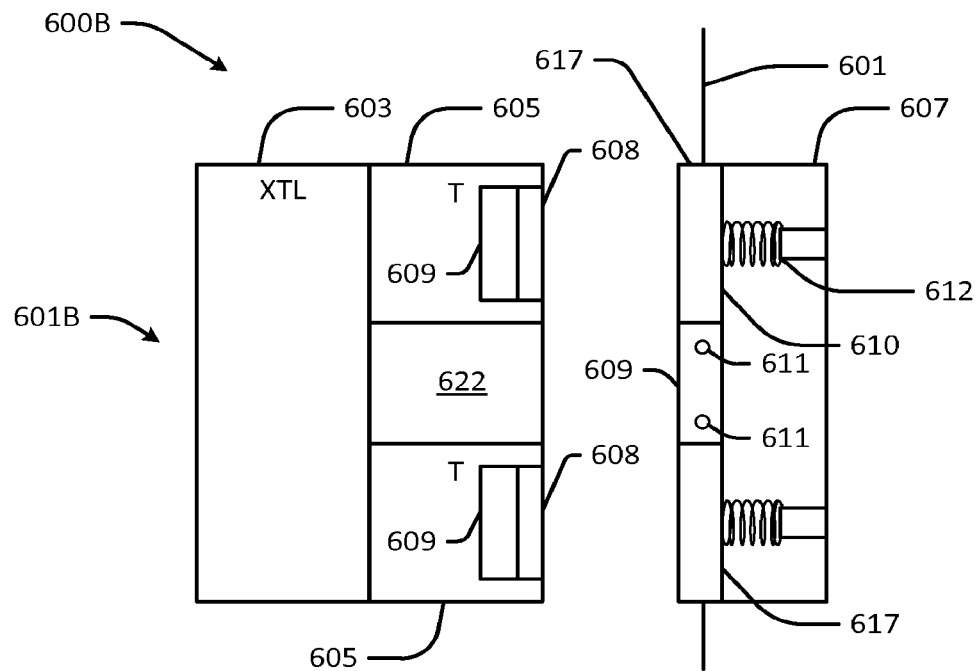
FIG. 9C shows a variation of the embodiment of FIGS. 9A and 9B in which elements for making two temperature measurements, one before a conductivity cell, and one after, according to embodiments of the disclosed subject matter.

FIG. 9C shows a variation of the embodiment of FIGS. 9A and 9B in which elements for making two temperature measurements, one before a conductivity cell 609, and one after. In the configuration of FIG. 9C, the module 607 combines two temperature measurement cells 617 with a single conductivity measurement cell 609. Temperature measurements are made prior to and following the conductance measurement and the temperature measurements may be averaged to ensure a more accurate temperature estimate during the conductance measurement in the event of any temperature change a fluid flowing through the line 601 while conductance is being measured. The elements labeled with like reference numerals are as described with reference to FIGS. 9A and 9B. Each of the conductivity/temperature measurement cells 610 and temperature measurement cells 617 may be of a somewhat flexible material which may be pressurized to allow fluid to flow through the cell while being urged against the insulator 608. Alternatively, each of the conductivity/temperature measurement cells 610 and temperature measurement cells 617 may be of a rigid material and the insulator 608 provided with a sufficiently compliant surface to ensure good and uniform thermal contact. In another variation, the latter embodiment may employ an intermediate material such as thermal grease or a thermal pad such as used to join heat sinks to solid state circuit packaging in electronic devices.

Figure 10A:
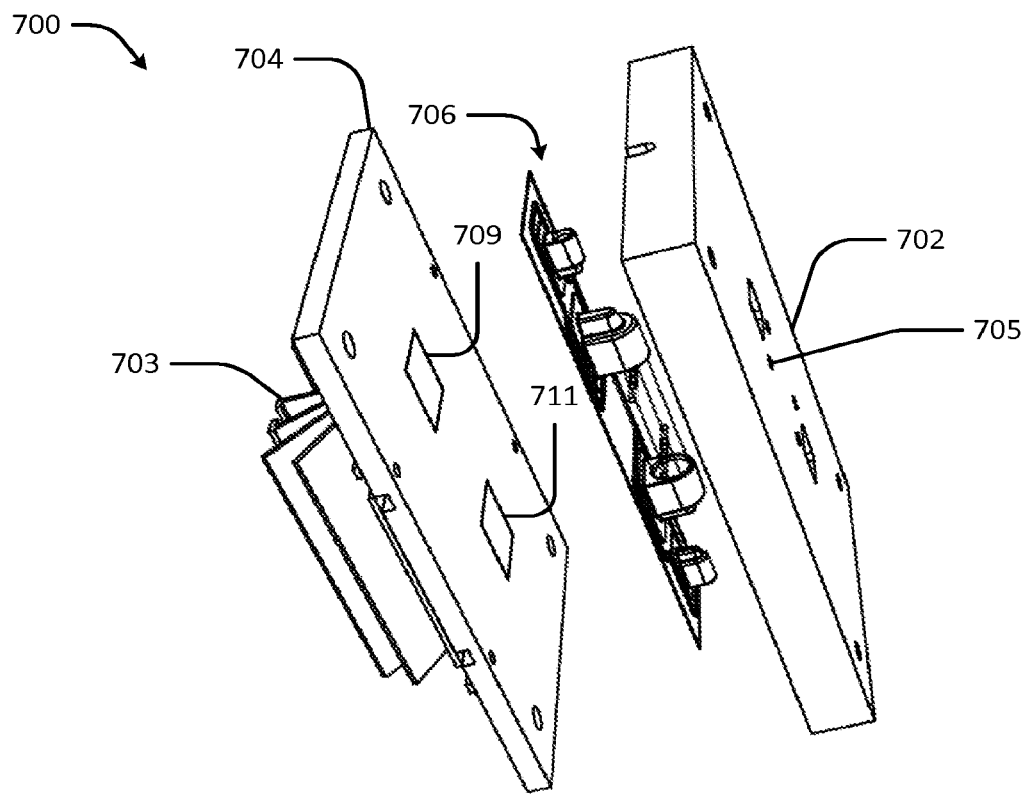
FIG. 10A shows a conductivity measurement device with a temperature measurement portion and a conductivity measurement portion, according to embodiments of the disclosed subject matter.
Figure 10B:
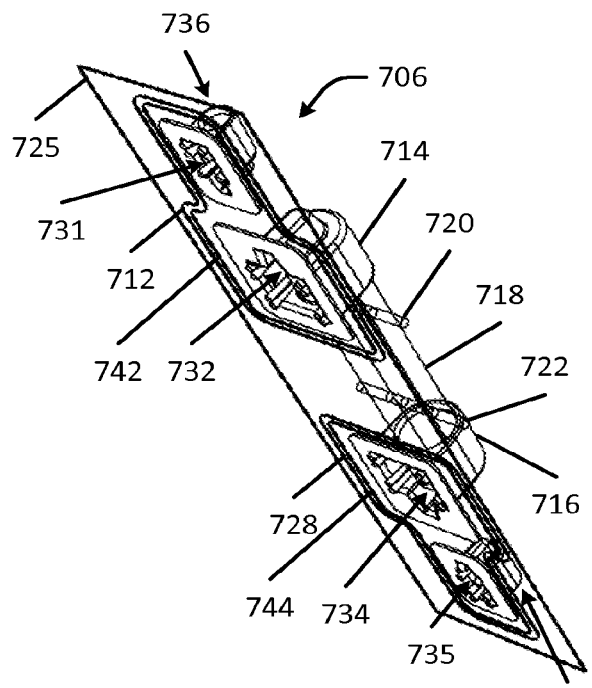
FIG. 10B shows details of a fluid channel portion which may form part of a disposable circuit, according to embodiments of the disclosed subject matter.

Referring to FIGS. 10A and 10B, FIG. 10A shows a conductivity measurement device 700 with a temperature measurement portion 704 and a conductivity measurement portion 702 that engage, by closing therearound, a disposable conductivity/temperature measurement cell 706 (shown also in FIG. 10B). The insulators 708 and 711 of active temperature detectors face, and contact, chambers 742 and 744. The temperature/conductivity measurement cell 706 engages with the temperature measurement portion 704 and the conductivity measurement portion 702 when they two are brought together around the conductivity measurement cell 706. The conductivity measurement cell 706 has a conductivity measurement column 718 with wetted conductors 720 and 722 which connect with contacts (not shown) in the conductivity measurement portion 702. A continuous flow path is defined between an inlet 736 and an outlet 738. The continuous flow path enters chamber 742 via elbow 714 through a first opening 731 leaves the chamber 742 through a second opening 732 leading to the conductivity measurement column 718 via elbow 714. Fluid leaves the conductivity measurement column 718 via elbow 716 and flows through opening 734 to pass into chamber 744 and then out through opening 735 where the flow exits through outlet 738. A pair of parallel panels 725 is seam welded as indicated at 712 and 728 to form the chambers 742 and 744. The panels are of material that provides some stiffness to support the conductivity measurement column 718 and the inlet 736 and 738 portions. The panels also provide sufficient flexibility to provide a conforming interface to the insulators 709 and 711.

The temperature measurement portion 704 and conductivity measurement portion 702 contain respective measurement circuits as described according to any of the disclosed embodiments. The temperature measurement portion 704 and conductivity measurement portion 702 close around, and engage, the conductivity measurement cell 706 to make thermal and electrical contact therewith. The conductivity measurement cell 706 may be permanently affixed to a fluid circuit, such as a medical treatment disposable circuit, for example, one for hemodialysis, peritoneal dialysis, treatment fluid preparation systems, etc. Conductivity measurement may be used in such systems for fluid property verification, for feedback-based preparation of target formulations, or for fluid property determination for any other purpose.

To make electrical contact between a conductivity measuring circuit and the wetted conductors 720 and 722, spring loaded contacts may be employed, one contacting each end of the electrode (each electrode 720 and 722 has two exposed ends). By using two contacts, for example, pogo pin type contacts, one at each end, a continuity test verifying contact with each pin (the continuity being between a first contact with one end of an electrode 720 or 722 and a second contact with the opposite end of the electrode 720 or 722) may serve as an indication that the disposable conductivity/temperature measurement cell 706 is properly positioned for use. The same continuity test can be done for both electrodes 720 and 722 and a control system may verify both continuity paths to confirm complete connection. It is noted that a regulated current source may be employed in conjunction with a high impedance voltage measurement device with the current applied at one end of each conductor and the voltage measurement made across the other end of each conductor. This is essentially a four-point conduction measurement which is not susceptible to the error which may be introduced by contact resistance in the voltage measurement. In this way, even if there is some contact resistance between the contacts and the electrodes 720 and 722, a predefined current will be established in the fluid column 718 of the cell whilst the high impedance voltage measurement will not be affected by the contact resistance. Thus, measurements will be reliable and accurate even in an instance where imperfect contact is made between the measuring circuit and one or both of the electrodes 720 and 722. Also, having provided dual contacts at each end of the conductivity cell column, the dual contacts are employed to determine, by continuity detection, if the conductivity cell is properly loaded. If continuity is not confirmed, an error signal may be generated and output by the system.

In additional system embodiments, the conductivity measurement may be used to verify the concentration of medicaments being supplied to a treatment system at the time of use. For example, at a time when a treatment system is being set-up, for example, a hemodialysis system, the dialysis fluid can flow into a conductivity detection system according to the disclosed embodiments, and a conductivity measurement compared to a prescription or other predefined indication of correct values or range of values. If the measurement fails to conform to the predefined range, an output can be generated to indicate the failure. Since the present system is capable of measuring temperature accurately, the conductivity measurements can be very precise and therefore they may indicate an attempt to use an incorrect prescription on a patient. An integrated system may also take automatic corrective action in response to an output indicating incorrect conductivity or concentration measurement.

In any of the embodiments, in addition to measuring conductance by means of wetted electrodes, other types of conductance (equivalently, resistance or resistivity) measurements may be employed, including contactless measuring devices, for example, magnetic induction devices may be employed for conductance measurement. Also, conductivity can be measured by devices that employ capacitive coupling as a means for measuring. Other specific technology for measuring conductance may also be employed.

An embodiment conforming to the general description of FIG. 5 and employing features of FIGS. 9A through 10B (as well as any others disclosed that are compatible) is an online medicament (e.g., dialysate) preparation device. An online system may have a mixing portion where the mixing ratios are continuously adjusted by a controller according to a feedback circuit providing conductivity measurement signal using the embodiments of FIGS. 9A through 10B and others. Such a system may have a disposable component to promote sterility and reduce the risk of contamination. A disposable component may have water filtration and mixing components in it. It may be desirable in such a system to generate the conductivity signal from the devices disclosed herein which provide highly accurate conductivity and temperature data to allow the concentration of medicament to be controlled, for example by feedback control. For example, the concentration of electrolytes in a medicament can be measured accurately with the conductivity and temperature signal provided by the present system. The synergy arises here because the accurate temperature measurement can be taken through the wall of disposable fluid circuit portion thereby to avoid the disruption of the circuit's sterile isolation from the outside environment or the inclusion of expensive additional components such as wetted temperature sensors. We note here that any of the features of the active temperature detectors may be incorporated in such a system as FIGS. 9A through 10B and others, such as those of FIGS. 11A through 14.

For example a system for generating a medicament may have a fluid circuit with a disposable portion. The fluid circuit may include a fluid conduction measuring portion and a temperature detecting portion as in any of the disclosed embodiments herein. The fluid circuit may have a mixing portion where the disposable portion is connected to convey a mixed product flowing from the mixing portion. A temperature detecting device according to any of the embodiments (including any of the claims) may be provided to contact with the disposable portion and measure a temperature of a mixed fluid flowing therethrough and to output a temperature signal. The conduction measuring portion may be configured to measure a conductivity of the mixed product flowing from the mixing portion and output a conductivity signal. A controller may be configured to control a relative flow of water and a concentrate into the mixing portion responsively to both of said temperature and conductivity signals. The controller may be configured for feedback control of a concentration of the mixed product. The controller may be configured to calculate, or look up in a data store, such as a memory or non-volatile data store, a parameter dependent on a concentration of the mixed product and to employ it as a negative feedback control signal to regulate concentration of said mixed product. Equivalently, the system is compensating the conduction signal using temperature so that and a concentration estimate or control signal can be generation.

Referring now to FIGS. 11A through 11C, an active temperature detector 800 has two temperature detectors 814, 816, for example resistance temperature detectors (RTDs) spaced apart along what approximates a one-dimensional thermal flow circuit in the configuration of active temperature detector 800. The temperature sensor 800 is configured such that it can be positioned adjacent the wall of a vessel/channel or fluid channel (not shown). For example, it may have a flat surface 812 against which the wall of a flexible flat vessel/channel or channel may be positioned or urged so that a predictable interface without a gap can be provided. In embodiments, the wall of a flexible channel or vessel/channel is urged by a positive static pressure therein.

The active temperature detector 800 includes a heating/cooling device 802 with a side 802B that exchanges heat with a thermal network and a side 802A that exchanges heat with an external medium, such as the ambient air. The heating/cooling device 802 may be of any suitable configuration as discussed elsewhere in the present application. In the illustrated embodiment, heating/cooling device 802 may be a thermoelectric heat pump or simply a dissipative heater. As stated, it could also be other kinds of suitable devices, for example any that can control the temperature of a side of the thermal network.

RTD-type temperatures detectors 816 and 817 may be spaced apart by an air gap 819. Although RTDs are discussed in the present embodiment, they could be replaced by any other type of temperature detector such as a thermistor, thermocouple, etc. In the present embodiment, a fluid-side RTD 816 is bonded or soldered to conductive pads on a flexible circuit member 818. A heating/cooling device-side RTD 816 is bonded or soldered to conductive pads on a flexible circuit member 820. The flexible circuit members 818 and 820 may be of any suitable material for carrying thin electrical leads, for example polyimide film used commonly in electrical systems. The flexible circuit members 818 and 820 material may be chosen to provide convenient flexible lead wires for making electrical connections. The flexible circuit members 818 and 820 need not be flexible and in embodiments may be made of rigid materials. A desirable property of the flexible circuit members 818 and 820 and variants of them is that their thermal properties do not vary significantly with mechanical load. Thus, a material whose conductivity and/or diffusivity is constant under various shear and pressure conditions as might attend normal use will provide consistent indications of temperature.

The air gap 819 is established by separating the flexible circuit members 818 and 820 by a spacer 808 which has an opening 814 to accommodate the RTDs 816 and 817. The flexible circuit members 818 and 820 may be adhesively bonded to the spacer 808. The spacer may be a monolithic or composite material, for example FR-4 commonly used in the electrical device industry. A desirable property of the spacer 808 and variants of it is that the thermal properties do not vary significantly with mechanical load.

A high thermal conductivity cup 805 has a recess 807 to receive the flexible circuit members 818 and 820 and spacer 808 assembly. The cup 805 ensures that a uniform temperature is applied to the non-fluid-side of the flexible circuit members 818 and 820 spacer 808 assembly by the heating/cooling device 802. For this purpose, the cup 805 may be of aluminum, copper, gold, or other suitable material. The arrangement, shape, and sizes of the flexible circuit members 818 and 820 spacer 808 assembly, including the bodies of the RTDs (which are generally platinum films mounted on a substrate) are chosen to ensure that the flow of heat at the center where the RTDs are located is normal to the surface 812. Thus, the spacer 808 should be sufficiently thermally insulating to provide a required low level of conductive heat transfer in a direction parallel to the surface 812.

Figure 11D:
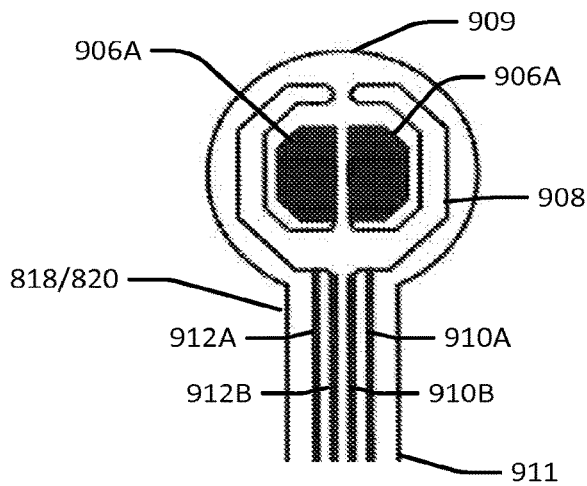
FIGS. 11D and 11E show wiring and structural features that may be used with various embodiments, for example, the active temperature detector permanent part of FIG. 11A, according to embodiments of the disclosed subject matter.
Figure 11E:
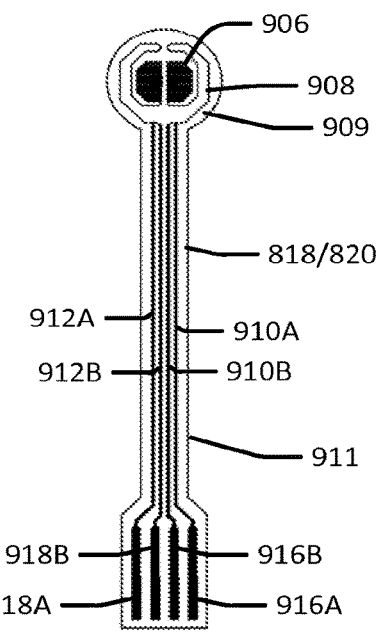

Referring now to FIGS. 11D and 11E, the RTDs may be attached to the flexible circuit members 818 and 820 by means of conductive attachment points 906A and 906B, which may be, for example, solder pads. Leads 908 may be provided, here defining elongate serpentine paths following a predominately circumferential course to help minimize thermal conduction in a radial direction, which would be diminish the desirable feature of a substantially one-dimensional thermal network in the region immediately around the RTDs. Two pairs of leads 910A, 910B and 912A, 912B with respective separate contact pads 916A, 916B and 918A, 918B may provide a mechanism for four point resistance measurement, which eliminates errors due to variations in system lead wire and electrical connector contact resistance. For example, two of the leads 916A and 918A may be used to drive a current and the other two may be connected to a high impedance voltage measurement device such that any voltage drop in the high current line will not affect the measurement of voltage drop across the temperature sensor connected between the pads conductive attachment points 906A and 906B.

In embodiments, the conductive attachment points 906A and 906B extend around the opening 814 and are suitably sized and of such material that they are sufficiently thermally conductive to ensure that the temperature across their faces are substantially uniform. This helps to ensure a one-dimensional heat transfer network is established, despite the high thermal resistance of the air gap between the temperature sensors that may exist. Another aspect of this construction is that the temperatures sensors (RTDs in this example butt they could be replaced by other types of temperature sensors) 816, 817 can be of a very different thermal conductivity than the spacer 808, without adding complexity or manufacturing variability to the feedback control mechanism upon which active temperature detection is based. Thus, the bodies of the temperature sensors 815, 817, if of highly thermally conductive material, such as a ceramic, may have a metal resistor (e.g., platinum) on any part thereof. Since they are positioned in an air gap and attached to the thermally conductive attachment points 906A and 906B, their temperatures are those of the attachment points 906A and 906B. Thus the thermal gradient is determined by the structure of the spacer 808 and it can be determined that it forms a simple thermal network whose properties are resistant to variability in the size, thermal properties, or other variability in the temperature sensor itself. Further, the manufacturing is simplified because the temperature sensors 815, 817 can be attached to the flexible circuit members 818 and 820 alone. The attachment to the spacer 808 is not a concern for manufacturing, for example as in embodiments in which the temperature sensors are embedded in the insulating material between them. In embodiments, an element other than the attachment points may provide for distributing heat across the spacer 808. For example, thermally conductive element may be attached to the spacer 808 or the flexible circuit elements to distribute heat. Such an element may be non-electrically conductive such as a ceramic.

It will be observed that the flexible circuit members 818 and 820 of FIGS. 11D and 11E embody a support for a temperature sensor in which electrical leads lead from temperature sensor attachment points at a center of an end portion 909. The following list of characterizations of the leads 909 may be implemented in any of the compatible embodiments described herein and others not specifically described but which may be enabled by the present disclosure. As well, these characterizations may describe features that are independent of the others in further embodiments.

- In embodiments, the end portion 909 is larger than an elongate portion 911 of the flexible circuit members 818 and 820.
- The electrical leads may be arranged in a manner that they take an indirect path from the end portion 909 to the elongate portion 911.
- The indirect path may be such that the leads 908 circumscribe, at least partly, the attachment points.
- The indirect path may be such that the leads 908 define serpentine paths.
- The indirect path may be such that the major portions of the leads 908 are curved.
- The indirect path may be such that the major portions of the leads 908 follow a path that is substantially tangential to a circumference of the end portion 909.
- The indirect path may be such that the major portions of the leads 908 double back on themselves.

Figure 11F:
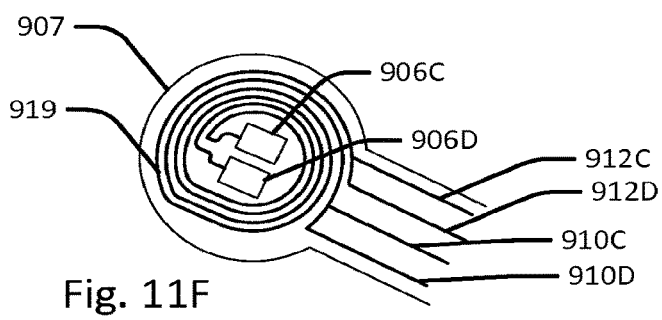
FIG. 11F shows a variant of the embodiment of FIGS. 11D, 11E, according to embodiments of the disclosed subject matter.

In the embodiment of FIG. 11F, the paths 919 are curved in a single direction and provide similar benefits to the paths shown in the previous embodiments for a flexible circuit member 907. Redundant sets of leads 910C, 910D and 912C, 912D and separate contact pads similar to 916A, 916B and 918AC, 918B may be provided for four-point resistance measurement as discussed above which help to reduce errors due to variations in lead and/or contact resistance.

Figure 12:
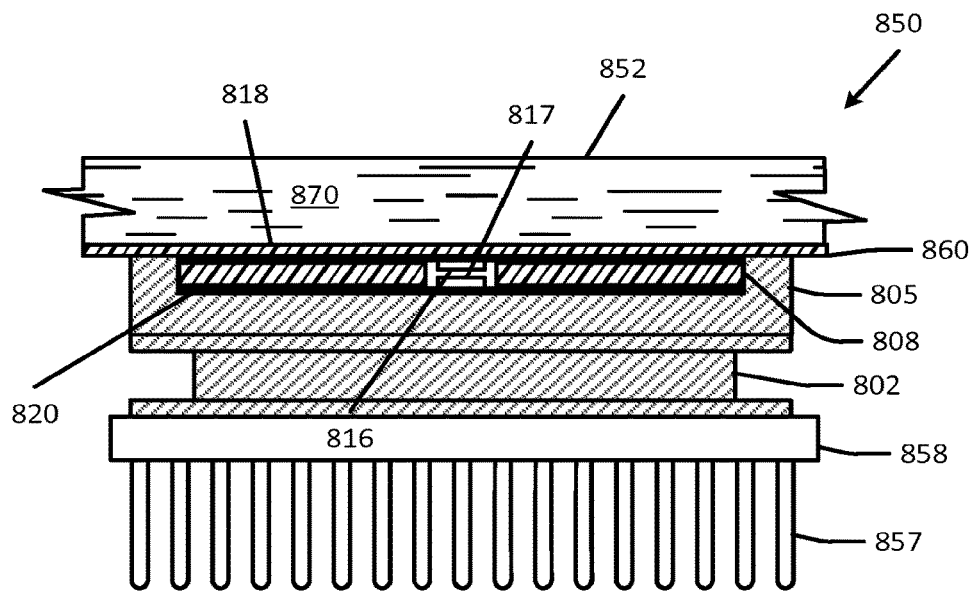
FIG. 12 a cross-section of an embodiment that includes all heat transfer and sensor aspects of a temperature measurement device according to embodiments of the disclosed subject matter.

Referring now to FIG. 12, an active temperature detector, for example one according to the description attending FIG. 11A through 11C, is shown cross section with a heat source/sink 858 having fins 857 and a vessel/channel wall 860. Thus FIG. 12 illustrates a complete thermal network as discussed above, connected thermally with the ambient on one end (heat sink) and with the fluid 870 whose temperature is measure at the other end. The elements shown in FIG. 12 are labeled using the same numerals as in FIGS. 11A through 11C so they are not identified again.

FIG. 13 shows a method for verifying thermal contact between an active temperature detector and a wall of a fluid vessel/channel according to embodiments of the disclosed subject matter. In embodiments, as described with reference to FIG. 5, a vessel/channel 306 is held against active temperature detector 314. To confirm contact between the active temperature detector 314 and the vessel/channel 306, a transient heat pulse is generated in one or more heat sources embedded in, or adjacent to, the active temperature detector 314 surface. The temperature response during heating or the temperature decay attending cooling (or both) of the relevant portion of the active temperature sensor 314 is/are then measured. For example, a time series of temperature measurements can be captured and stored. Preferably the temperature of a surface portion as close as possible to the vessel/channel 306 wall is measured. By comparing the thermal response of the measured temperature to a predicted temperature decay profile. This may be done numerically or by finding the parameters that best fit a curve, such as an exponential or Gaussian, or straight-line fit to a logarithmic plot to a time series of temperature measurements. Known techniques for measuring conductivity and/or diffusivity can be adapted for determining the quality of the thermal contact so the details are not elaborated here. Uniform and direct contact between the vessel/channel 306 and the surface of the temperature detector 314 can be distinguished by a purely empirical approach as well. A slow decay indicates that the thermal contact between the active temperature detector is poor whilst a rapid decay indicates good thermal contact. In alternative embodiments, time series of temperature measurements are obtained during a heating, or the combined temperature profile of heating and cooling (recovery) are sampled. Note that the method of FIG. 13 may be practiced apart from the embodiment of FIG. 5. The technique described above can be used in passive as well as active temperature detectors.

In a system embodiment, a controller may be used to implement the method of FIG. 13. Referring now to FIG. 13, at S10, a fluid circuit portion is positioned adjacent the active temperature detector. At S12, a transient thermal pulse is generated. The same device used for measuring temperature may also be used for measuring temperature. For example, a wire or film of an RTD may be used to dissipate thermal energy in the temperature detector. A suitably designed thermocouple or thermistor may be used to generate heat as well. In embodiments, a film or wire immediately adjacent the vessel/channel wall is present in the active temperature sensor. The transient thermal event may be generated by a different device from that used to determine temperature. One or more temperature sensor, heat elements, or combinations thereof may be provided for this purpose. At S14, a time series of temperatures are recorded. If multiple sensors are used, then multiple series may be sampled and recorded. At S16, the measured time-temperature data are compared to a predetermined model or template and at S18, a determination is made whether the data fit a desirable profile or an undesirable profile. If the profile indicates the fit is in a desired range, an indication (such as a digital signal) of an acceptable configuration is generated at S20, otherwise an indication (such as a digital signal) of an unacceptable configuration is generated. The signals may be output to a display, for example, a message to request an operator to fix the mechanical engagement of the fluid circuit with the vessel/channel with the temperature detector, to replace the fluid circuit with the vessel/channel, or take some other action.

FIG. 14 shows an active temperature detector with features for verifying thermal contact between a surface thereof and a wall of a fluid vessel/channel according to embodiments of the disclosed subject matter. A 909 flexible circuit element 950 end portion 951 has an array of temperature sensors 954 and a center temperature sensor 956 which are all wired to contact pads 964 on a dependent portion 952 thereof. As in earlier-described embodiments, the flexible circuit element may have only a single temperature sensor 956. The embodiment illustrated shows multiple temperature sensors which can verify good thermal contact as described above by energizing each, simultaneously or consecutively a combination thereof and monitoring the transient temperature. The circuit leads have various features such as serpentine bends 962 and 958 as well as elongate paths that run in generally circumferential directions to minimize thermal conduction as discussed above.

Variations of the above embodiments may be formed by providing other shapes of surfaces that define different heat flow paths which may be reliably modeled in order to extrapolate a temperature at a location of the heat flow path from two or more temperature measurements. For example, an active temperature detector may be configured as a cylindrical or spherical heat source with temperature sensors spaced radially apart in a medium whose heat transfer properties can be modeled or are repeatable after calibration.

In any of the above embodiments, a system may be configured to guarantee that a positive static pressure in a flow channel or vessel/channel with flexible walls is provided. This may ensure good thermal contact between the fluid volume whose temperature is to be measured is consistent with the model used for extrapolation of the temperature of the fluid. The system may also be provided with a mechanism, such as a stirrer, to ensure the fluid temperature is uniform. In addition, in embodiments in which there is a fluid that flows through a channel whose temperature is to be measured, the channel may be configured to guarantee that the flow does not stagnate whose temperature is uniform across the interfacing surface of the active temperature detector. This feature may be applied in any of the embodiments. For this purpose, for example, flow guides may help to distribute flow in an expanding section of the fluid circuit to ensure there are no stagnating regions and that all flow cross-sections carry flow. In embodiments, the flow mass rate may be uniform across the region that coincides with the contact surface of the active temperature detector.

It will be appreciated that the modules, processes, systems, and sections described above can be implemented in hardware, hardware programmed by software, software instruction stored on a non-transitory computer-readable medium or a combination of the above. For example, a method for measuring temperature can be implemented, for example, using a processor configured to execute a sequence of programmed instructions stored on a non-transitory computer-readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C #.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors, or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their subcomponents or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer-readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of heat transfer and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, active temperature measurement methods, devices and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention, examples of which are described below.

According to first embodiments, the disclosed subject matter includes a vessel/channel with a temperature detecting device. A first temperature sensor is attached to or placed against a wall of a vessel/channel configured for carrying or containing a fluid. A second temperature sensor is separated from the first temperature sensor by an insulating body having a thermal resistance similar to the vessel/channel wall. A temperature regulating device is in thermal contact with the second temperature sensor and configured to receive first and second temperature indication signals, respectively, from the first and second temperature sensors. The temperature regulating device is further configured to minimize a difference in temperatures indicated by the first and second temperature signals by regulating a rate of flow of heat between the first and second temperature sensors.

The first embodiments may be revised to form further first embodiments. For example, in such embodiments, the temperature regulating device includes a thermoelectric heat pump. The first embodiments may be revised to form still further first embodiments. For example, in such embodiments, the temperature regulating device includes a dissipative heater. The first embodiments may be revised to form still further first embodiments. For example, in such embodiments, the second temperature sensor and or the heat controlling device have a surface that extends beyond the surface of the first temperature sensor. The first embodiments may be revised to form still further first embodiments. For example, in such embodiments, the insulating body fills the empty space between the second temperature sensor and the fluid vessel/channel wall. The first embodiments may be revised to form still further first embodiments. For example, in such embodiments, the vessel/channel is a bag or flexible membrane configured to contain a medicament, a biological fluid such as blood or plasma, or a fluid circuit configured to convey a medicament, a biological fluid such as blood or plasma.

According to second embodiments, the disclosed subject matter includes a temperature detecting device with an insulating member with a first surface and temperature sensor configured to be attached to or placed against a wall of a vessel/channel carrying or containing a fluid, the temperature sensor being configured to measure a temperature the first surface. A heat flux sensor is configured to detect heat flow between the surface and a second surface of the insulating body opposite the first surface. A temperature regulating device is in thermal contact with the second surface. A controller regulates the temperature regulating device responsively to the heat flux sensor to minimize a flux. The controller is further configured to generate a command to sample temperature measurements when a predefined flux level is detected.

The second embodiments may be revised to form further second embodiments. For example, in such embodiments, the temperature regulating device includes a thermoelectric heat pump. The second embodiments may be revised to form further second embodiments. For example, in such embodiments, the temperature regulating device includes a dissipative heater. The second embodiments may be revised to form further second embodiments. For example, in such embodiments, the insulator member first surface has a major dimension that is larger than a distance between the first and second surfaces. The second embodiments may be revised to form further second embodiments. For example, in such embodiments, the insulating member is of a material with thermal conductivity that is approximately the same as that of the wall.

According to third embodiments, the disclosed subject matter includes a system for measuring electrical conductivity, a fluid conduction measuring circuit, a temperature measuring element, and a controller configured to control the conduction measuring circuit and the temperature measuring element. The temperature measuring element has at least one thermal contact portion with a temperature sensor and a temperature measuring circuit and a fluid circuit is configured to carry a fluid, the fluid circuit including a wetted conductor inside a conductivity cell portion, the wetted conductor having a having a contact, external to the fluid circuit, for interfacing with the conduction measuring circuit. The fluid circuit includes at least one temperature measurement portion having predefined thermal properties and configured to touch the thermal contact portion. The controller is configured to control the temperature measuring element and the conduction measuring circuit to generate and output at least one set of contemporaneous temperature and conduction measurements.

The third embodiments may be revised to form further third embodiments. For example, in such embodiments, the temperature measuring element includes an active temperature regulator configured to apply heat to or draw heat from the contact portion. The third embodiments may be revised to form further third embodiments. For example, in such embodiments, the temperature measuring element includes an active temperature regulator configured to apply heat to or draw heat from the contact portion and the controller is configured to regulate the temperature regulator so as to nullify heat flow through a wall of the temperature measurement portion. The third embodiments may be revised to form further third embodiments. For example, in such embodiments, the controller is configured to derive a fluid property algorithm or database responsively to the contemporaneous temperature and conduction measurements.

According to fourth embodiments, the disclosed subject matter includes a method for measuring electrical conductivity that includes flowing a fluid through a chamber and then over a pair of conductors while applying a regulated current between the conductors and measuring a voltage thereacross to obtain a conductance measurement of the fluid, contacting the chamber with an external temperature measuring device and sampling temperature measurements therefrom, and compensating or nullifying a flow of thermal energy through a wall of the chamber in order to obtain a temperature measurement estimate of the fluid. The method further includes combining the temperature measurement estimate and conductance measurement to estimate a property of the fluid.

According to fifth embodiments, the disclosed subject matter includes a temperature detecting device that includes a first temperature sensor attached to a flat member that is adapted to be placed against a wall of a vessel/channel configured for carrying or containing a fluid. A second temperature sensor is separated from the first temperature sensor by an insulating gap. A temperature regulating device is in thermal contact with the second temperature sensor. A controller is configured to receive first and second temperature indication signals, respectively, from the first and second temperature sensors and to regulate the temperature regulating device responsively to signals therefrom. The controller is configured to regulate a heat flux rate through the flat member responsively to the signals from the first and second temperature sensors such that a temperature of at least the first temperature sensor indicates a temperature of a fluid on an a side of the wall opposite the first temperature sensor.

The fifth embodiments may be revised to form further fifth embodiments. For example, in such embodiments, the temperature regulating device includes a thermoelectric heat pump. The fifth embodiments may be revised to form further fifth embodiments. For example, in such embodiments, the temperature regulating device includes a dissipative heater. The fifth embodiments may be revised to form further fifth embodiments. For example, in such embodiments, the second temperature sensor and or the heat controlling device have a surface that extends beyond the surface of the first temperature sensor. The fifth embodiments may be revised to form further fifth embodiments. For example, in such embodiments, the gap includes an insulating body between the first and second temperature sensors. The fifth embodiments may be revised to form further fifth embodiments. For example, in such embodiments, the vessel/channel is a bag or flexible membrane configured to contain a medicament, a biological fluid such as blood or plasma, or a fluid circuit configured to convey a medicament, a biological fluid such as blood or plasma. The fifth embodiments may be revised to form further fifth embodiments. For example, in such embodiments, a metal or other high thermal conductivity member may be provided adjacent the second temperature sensor adapted for maintaining a uniform temperature across the temperature regulating device.

According to sixth embodiments, the disclosed subject matter includes temperature detecting device with a first temperature sensor attached to a first flat member that is adapted to be placed against a wall of a vessel/channel configured for carrying or containing a fluid and a second temperature sensor attached to a second flat member separated from the first temperature sensor by a spacer. A temperature regulating device is in thermal contact with the second flat member opposite the second temperature sensor. A controller is configured to receive first and second temperature indication signals, respectively, from the first and second temperature sensors and to regulate the temperature regulating device responsively to signals therefrom. The controller is configured to regulate the heat flux rate through the flat member responsively to the signals from the first and second temperature sensors such that a temperature of at least the first temperature sensor indicates a temperature of a fluid on an a side of the wall opposite the first temperature sensor.

The sixth embodiments may be revised to form further sixth embodiments. For example, in such embodiments, the temperature regulating device includes a thermoelectric heat pump. The sixth embodiments may be revised to form further sixth embodiments. For example, in such embodiments, the temperature regulating device includes a dissipative heater. The sixth embodiments may be revised to form further sixth embodiments. For example, in such embodiments, the second temperature sensor and or the heat controlling device have a surface that extends beyond the surface of the first temperature sensor. The sixth embodiments may be revised to form further sixth embodiments. For example, in such embodiments, the gap includes an insulating body between the first and second temperature sensors. The sixth embodiments may be revised to form further sixth embodiments. For example, in such embodiments, the vessel/channel is a bag or flexible membrane configured to contain a medicament, a biological fluid such as blood or plasma, or a fluid circuit configured to convey a medicament, a biological fluid such as blood or plasma. The sixth embodiments may be revised to form further sixth embodiments. For example, in such embodiments a high thermal conductivity member may be provided adjacent the second temperature sensor adapted for maintaining a uniform temperature across the temperature regulating device. The sixth embodiments may be revised to form further sixth embodiments. For example, in such embodiments, the first and second flat members carry conductors that make electrical contact between the temperature sensors and the controller. The sixth embodiments may be revised to form further sixth embodiments. For example, in such embodiments, the flat members have end portions that are wider than an elongate portion thereof. The sixth embodiments may be revised to form further sixth embodiments. For example, in such embodiments, a spacer may be sandwiched between the flat member end portions and effective for spacing the temperature sensors apart. The sixth embodiments may be revised to form further sixth embodiments. For example, in such embodiments, the spacer has an opening in the center thereof such that an air gap is defined between the temperature sensors. The sixth embodiments may be revised to form further sixth embodiments. For example, in such embodiments, a spacer is sandwiched between the flat members and effective for spacing the temperature sensors apart. The sixth embodiments may be revised to form further sixth embodiments. For example, in such embodiments, the electrical leads are arranged in a manner that they take an indirect path from an end portion of the elongate members whereby thermal conduction from the temperature sensors in a radial direction is minimized. The sixth embodiments may be revised to form further sixth embodiments. For example, in such embodiments, the indirect path paths are such that the leads circumscribe, at least partly, the temperature sensors. The sixth embodiments may be revised to form further sixth embodiments. For example, in such embodiments, the indirect path paths are such that the leads are serpentine. The sixth embodiments may be revised to form further sixth embodiments. For example, in such embodiments, the indirect path paths are curved around the temperature sensors. The sixth embodiments may be revised to form further sixth embodiments. For example, in such embodiments, the electrical leads are arranged in a manner that they take an indirect path from an end portion of the elongate members whereby thermal conduction from the temperature sensors in a radial direction is minimized. The sixth embodiments may be revised to form further sixth embodiments. For example, in such embodiments, the indirect path paths are such that the leads circumscribe, at least partly, the temperature sensors. The sixth embodiments may be revised to form further sixth embodiments. For example, in such embodiments, the indirect path paths are such that the leads are serpentine. The sixth embodiments may be revised to form further sixth embodiments. For example, in such embodiments, the indirect path paths are curved around the temperature sensors. The sixth embodiments may be revised to form further sixth embodiments. For example, in such embodiments, the end portions are substantially round and major portions of the leads follow a path that is substantially tangential to a circumference of the end portions. The sixth embodiments may be revised to form further sixth embodiments. For example, in such embodiments, the indirect path may be such that the major portions of the leads double back on themselves.

According to seventh embodiments, the disclosed subject matter includes a system for measuring electrical conductivity that has a fluid electrical resistance measuring circuit, a temperature measuring element, and a controller configured to control the fluid electrical resistance measuring circuit and the temperature measuring element. The temperature measuring element has at least one thermal contact portion with a temperature sensor and a temperature measuring circuit. A fluid circuit is configured to carry a fluid, the fluid circuit includes capacitive and/or induction coupling portions to permit resistance measurement of a fluid inside a resistivity cell portion, the capacitive and/or induction coupling portions being connected to a resistance measurement circuit for measuring resistance through the capacitive and/or induction coupling portions, for interfacing with the fluid resistance measuring circuit. The fluid circuit includes at least one temperature measurement portion has predefined thermal properties and configured to touch the thermal contact portion. The controller is configured to control the temperature measuring element and the fluid resistance measuring circuit to generate and output at least one set of contemporaneous temperature and conduction measurements.

The seventh embodiments may be revised to form further seventh embodiments. For example, in such embodiments, the temperature measuring element includes an active temperature regulator configured to apply heat to or draw heat from the contact portion. The seventh embodiments may be revised to form further seventh embodiments. For example, in such embodiments, the temperature measuring element includes an active temperature regulator configured to apply heat to or draw heat from the contact portion and the controller is configured to regulate the temperature regulator so as to nullify heat flow through a wall of the temperature measurement portion. The seventh embodiments may be revised to form further seventh embodiments. For example, in such embodiments, the controller is configured to derive a fluid property algorithm or database responsively to the contemporaneous temperature and resistance measurements.

According to eight embodiments, the disclosed subject matter includes a fluid management system with a temperature detecting device. A fluid circuit has a pump and a controller adapted for controlling the flow of fluid in the fluid circuit. A temperature detector is controlled by the controller. The temperature detector has a first temperature sensor, attached to or placed against a wall of a portion of the fluid circuit and a second temperature sensor separated from the first temperature sensor by an insulating body has a thermal resistance similar to the portion wall. A temperature regulating device is in thermal contact with the second temperature sensor and configured to receive first and second temperature indication signals, respectively, from the first and second temperature sensors. The temperature regulating device is further configured to minimize a difference in temperatures indicated by the first and second temperature signals by regulating a rate of flow of heat between the first and second temperature sensors. The controller is further configured to control the temperature regulating device to regulate the flow of heat between the first and second temperature sensors flow of fluid responsively to a signal indicating the presence of a predetermined minimum flow in the fluid circuit portion.

The eighth embodiments may be revised to form further eighth embodiments. For example, in such embodiments, the temperature regulating device includes a thermoelectric heat pump. The eighth embodiments may be revised to form further eighth embodiments. For example, in such embodiments, the temperature regulating device includes a dissipative heater. The eighth embodiments may be revised to form further eighth embodiments. For example, in such embodiments, the second temperature sensor and or the temperature regulating device has a surface that extends beyond the surface of the first temperature sensor. The eighth embodiments may be revised to form further eighth embodiments. For example, in such embodiments, the insulating body fills the empty space between the second temperature sensor and the fluid wall portion. The eighth embodiments may be revised to form further eighth embodiments. For example, in such embodiments, the wall portion is a part of a bag or flexible membrane configured contain or channel a flow of medicament or a biological fluid such as blood or plasma. The eighth embodiments may be revised to form further eighth embodiments. For example, in such embodiments, a thermal conductivity of the insulating body is substantially the same as a thermal conductivity of the portion wall. The eighth embodiments may be revised to form further eighth embodiments. For example, in such embodiments, the insulating body has an air gap in a center thereof and the first and second temperature sensors are separated across the air gap.

According to ninth embodiments, the disclosed subject matter includes an active temperature detector with an insulator having at least one temperature sensor. A heat flux regulation element heats or cools a first side of the insulator, responsively to one or more first temperature sensors, so as to maintain a condition of zero heat flux under steady state conditions when a target member is brought into contact with a second side of the insulator, the second side being opposite the first side. A controller is configured to generate a transient temperature change in one or more second temperature sensors and/or the heat flux regulation element and to store temperature samples indicated by one or more second temperature sensors over a time interval coinciding with, or following, the transient temperature change. The controller is further configured to generate a control signal indicating a characteristic of the thermal contact between the target member and the insulator responsively to the stored temperature samples.

The ninth embodiments may be revised to form further ninth embodiments. For example, in such embodiments, the target member is a portion of a fluid circuit. The ninth embodiments may be revised to form further ninth embodiments. For example, in such embodiments, the target member is a portion of a fluid-containing vessel or channel. The ninth embodiments may be revised to form further ninth embodiments. For example, in such embodiments, the target member is a portion of a fluid circuit of a medical treatment device. The ninth embodiments may be revised to form further ninth embodiments. For example, in such embodiments, the target member is a flexible panel of a fluid circuit of a medical treatment device. The ninth embodiments may be revised to form further ninth embodiments. For example, in such embodiments, the heat flux regulation element includes a thermoelectric heating/cooling device. The ninth embodiments may be revised to form further ninth embodiments. For example, in such embodiments, the heat flux regulation element includes a dissipative heater. The ninth embodiments may be revised to form further ninth embodiments. For example, in such embodiments, the at least one temperature sensor includes at least two temperature sensors. The ninth embodiments may be revised to form further ninth embodiments. For example, in such embodiments, the first one or more temperature sensors are the same as the second one or more temperature sensors. The ninth embodiments may be revised to form further ninth embodiments. For example, in such embodiments, the first one or more temperature sensors are different from the second one or more temperature sensors. The ninth embodiments may be revised to form further ninth embodiments. For example, in such embodiments, the first one or more temperature sensors includes at least two temperature sensors and one of them is the second one or more temperature sensors. The ninth embodiments may be revised to form further ninth embodiments. For example, in such embodiments, the control signal is output to a user interface adapted to indicate the characteristic. The ninth embodiments may be revised to form further ninth embodiments. For example, in such embodiments, the characteristic indicates whether there is an air gap between the insulator and the target member. The ninth embodiments may be revised to form further ninth embodiments. For example, in such embodiments, the controller is configured to generate the transient temperature change by driving a current through one of the one or more second temperature sensors.

According to tenth embodiments, the disclosed subject matter includes an active temperature detector with an insulator with at least one temperature sensor. a heat flux regulation element that heats or cools a first side of the insulator, responsively to temperature sensors attached to the insulator, so as to maintain a condition of zero heat flux under steady state conditions when a target member is brought into contact with a second side of the insulator, the second side being opposite the first side. A controller is configured to generate a transient temperature change by driving a current through one of the temperature sensors or the heat flux regulation element and to store temperature samples indicated by one of the temperature sensors over a time interval coinciding with, or following, the transient temperature change. The controller is further configured to generate a control signal indicating a characteristic of the thermal contact between the target member and the insulator responsively to the stored temperature samples.

The tenth embodiments may be revised to form further tenth embodiments. For example, in such embodiments, the target member is a portion of a fluid circuit of a medical treatment device. The tenth embodiments may be revised to form further tenth embodiments. For example, in such embodiments, the target member is a portion of a fluid circuit. The tenth embodiments may be revised to form further tenth embodiments. For example, in such embodiments, the target member is a portion of a fluid-containing vessel or channel. The tenth embodiments may be revised to form further tenth embodiments. For example, in such embodiments, the target member is a portion of a fluid circuit of a medical treatment device. The tenth embodiments may be revised to form further tenth embodiments. For example, in such embodiments, the target member is a flexible panel of a fluid circuit of a medical treatment device. The tenth embodiments may be revised to form further tenth embodiments. For example, in such embodiments, the heat flux regulation element includes a thermoelectric heating/cooling device. The tenth embodiments may be revised to form further tenth embodiments. For example, in such embodiments, the heat flux regulation element includes a dissipative heater. The tenth embodiments may be revised to form further tenth embodiments. For example, in such embodiments, the control signal is output to a user interface adapted to indicate the characteristic. The tenth embodiments may be revised to form further tenth embodiments. For example, in such embodiments, the characteristic indicates whether there is an air gap between the insulator and the target member. The tenth embodiments may be revised to form further tenth embodiments. For example, in such embodiments, the controller is configured to generate the transient temperature change by driving a current through one of the one or more second temperature sensors.

According to eleventh embodiments, disclosed subject matter includes a temperature detecting device with a first temperature sensor attached to an interface member that is adapted to be placed against a wall of a vessel/channel configured for carrying or containing a fluid. A second temperature sensor is separated from the first temperature sensor by an insulating gap. a temperature regulating device in thermal contact with interface member and closer to the second temperature sensor then the first temperature sensor. A controller is configured to receive first and second temperature indication signals, respectively, from the first and second temperature sensors and to regulate the temperature regulating device responsively to signals therefrom. The controller is configured to regulate a heat flux rate through the interface member responsively to the signals from the first and second temperature sensors such that a temperature of at least the first temperature sensor indicates a temperature of a fluid on a side of the wall opposite the first temperature sensor.

The eleventh embodiments may be revised to form further eleventh embodiments. For example, in such embodiments, the temperature regulating device includes a thermoelectric heat pump. The eleventh embodiments may be revised to form further eleventh embodiments. For example, in such embodiments, the temperature regulating device includes a dissipative heater. The eleventh embodiments may be revised to form further eleventh embodiments. For example, in such embodiments, the second temperature sensor and or the heat controlling device have a surface that extends beyond the surface of the first temperature sensor. The eleventh embodiments may be revised to form further eleventh embodiments. For example, in such embodiments, the gap includes an insulating body between the first and second temperature sensors. The eleventh embodiments may be revised to form further eleventh embodiments. For example, in such embodiments, the vessel/channel is a bag or flexible membrane configured to contain a medicament, a biological fluid such as blood or plasma, or a fluid circuit configured to convey a medicament, a biological fluid such as blood or plasma. The eleventh embodiments may be revised to form further eleventh embodiments. For example, in such embodiments, a metal member is adjacent the second temperature sensor adapted for maintaining a uniform temperature across the temperature regulating device. The eleventh embodiments may be revised to form further eleventh embodiments. For example, in such embodiments, the gap includes an air gap between the first and second temperature sensors. The eleventh embodiments may be revised to form further eleventh embodiments. For example, in such embodiments, the interface member has a surface that is of a complementary shape to a surface of the wall effective to ensure uniform thermal resistance over an interfacing area therebetween. The eleventh embodiments may be revised to form further eleventh embodiments. For example, in such embodiments, the wall is flexible and the interface member has a smooth surface to which the wall is conformable such that a thermal resistance over an interfacing area therebetween is uniform. The eleventh embodiments may be revised to form further eleventh embodiments. For example, in such embodiments, the wall is one of concave and convex and the interface member has an interfacing surface that interfaces with the wall that is the other of concave and convex, such that a thermal resistance over an interfacing area therebetween is uniform. The eleventh embodiments may be revised to form further eleventh embodiments. For example, in such embodiments, the interface member has an identical shape to a surface of the wall effective to ensure uniform thermal resistance over an interfacing area therebetween. The eleventh embodiments may be revised to form further eleventh embodiments. For example, in such embodiments, the wall of a vessel/channel is a part of a fluid circuit of a medical treatment device.

According to twelfth embodiments, the disclosed subject matter includes a temperature detecting device with a first temperature sensor attached to a first flat member that is adapted to be placed against a wall of a vessel/channel configured for carrying or containing a fluid. A second temperature sensor is attached to a second flat member separated from the first temperature sensor by a spacer. the spacer has openings in a center thereof in which the first and second temperature sensors are received. the first and second flat members being attached to the spacer such that the first and second temperature sensors are attached indirectly through the first and second flat member, respectively, to the spacer.

The twelfth embodiments may be revised to form further twelfth embodiments. For example, in such embodiments, an air gap separates the first and second sensors. The twelfth embodiments may be revised to form further twelfth embodiments. For example, in such embodiments, the spacer and temperature sensors are not directly attached. The twelfth embodiments may be revised to form further twelfth embodiments. For example, in such embodiments, the first and second flat members are bonded to the spacer. The twelfth embodiments may be revised to form further twelfth embodiments. For example, in such embodiments, a temperature regulating device is in thermal contact with the second flat member opposite the second temperature sensor; a controller configured to receive first and second temperature indication signals, respectively, from the first and second temperature sensors and to regulate the temperature regulating device responsively to signals therefrom; the controller being configured to regulate the a heat flux rate through the flat member responsively to the signals from the first and second temperature sensors such that a temperature of at least the first temperature sensor indicates a temperature of a fluid on an a side of the wall opposite the first temperature sensor. The twelfth embodiments may be revised to form further twelfth embodiments. For example, in such embodiments, the temperature regulating device includes a thermoelectric heat pump or a dissipative heater. The twelfth embodiments may be revised to form further twelfth embodiments. For example, in such embodiments, the spacer and first and second flat members are adhesively or thermally bonded together. The twelfth embodiments may be revised to form further twelfth embodiments. For example, in such embodiments, the second temperature sensor and or the heat controlling device have a surface that extends beyond the surface of the first temperature sensor. The twelfth embodiments may be revised to form further twelfth embodiments. For example, in such embodiments, the vessel/channel is a bag or flexible membrane configured to contain a medicament, a biological fluid such as blood or plasma, or a fluid circuit configured to convey a medicament, a biological fluid such as blood or plasma. The twelfth embodiments may be revised to form further twelfth embodiments. For example, in such embodiments, a metal heat transfer member of Aluminum Nitride, Beryllium Oxide is adjacent the second temperature sensor adapted for maintaining a uniform temperature across the temperature regulating device. The twelfth embodiments may be revised to form further twelfth embodiments. For example, in such embodiments, the first and second flat members carry conductors that make electrical contact between the temperature sensors and the controller. The twelfth embodiments may be revised to form further twelfth embodiments. For example, in such embodiments, the flat members have end portions that are wider than an elongate portion thereof. The twelfth embodiments may be revised to form further twelfth embodiments. For example, in such embodiments, the spacer has an opening in the center thereof such that an air gap is defined between the temperature sensors. The twelfth embodiments may be revised to form further twelfth embodiments. For example, in such embodiments, the first and second flat members have electrical leads arranged in a manner that they take an indirect path from an end portion of the elongate members whereby thermal conduction from the temperature sensors in a radial direction is minimized. The twelfth embodiments may be revised to form further twelfth embodiments. For example, in such embodiments, the indirect path paths are such that the leads circumscribe, at least partly, the temperature sensors. The twelfth embodiments may be revised to form further twelfth embodiments. For example, in such embodiments, the indirect path paths are such that the leads are serpentine. The twelfth embodiments may be revised to form further twelfth embodiments. For example, in such embodiments, the indirect path paths are curved around the temperature sensors. The twelfth embodiments may be revised to form further twelfth embodiments. For example, in such embodiments, the first and second flat members have electrical leads arranged in a manner that they take an indirect path from an end portion of the elongate members whereby thermal conduction from the temperature sensors in a radial direction is minimized. The twelfth embodiments may be revised to form further twelfth embodiments. For example, in such embodiments, the indirect path paths are such that the leads circumscribe, at least partly, the temperature sensors. The twelfth embodiments may be revised to form further twelfth embodiments. For example, in such embodiments, the indirect path paths are such that the leads are serpentine. The twelfth embodiments may be revised to form further twelfth embodiments. For example, in such embodiments, the indirect path paths are curved around the temperature sensors. The twelfth embodiments may be revised to form further twelfth embodiments. For example, in such embodiments, the end portions are substantially round and major portions of the leads follow a path that is substantially tangential to a circumference of the end portions. The twelfth embodiments may be revised to form further twelfth embodiments. For example, in such embodiments, the indirect path may be such that the major portions of the leads double back on themselves. The twelfth embodiments may be revised to form further twelfth embodiments. For example, in such embodiments, the heat transfer member includes one or both of Aluminum Nitride and Beryllium Oxide.

It will be apparent to those of skill in the art that a feature of the active temperature detector embodiments disclosed above is an insulator with at least one temperature sensor, a heat flux regulation element that heats or cools a first side of said insulator, responsively to the at least one temperature sensor, so as to maintain a condition of zero heat flux under steady state conditions when a target member, such as a fluid channel or vessel, is brought into contact with a second side of said insulator where the second side being opposite said first side.

What is claimed is:

1. A system for generating a medicament, comprising:
a fluid circuit having a disposable portion;
a fluid conductivity measuring portion configured to measure a conductivity of a mixed product flowing through the disposable portion and to output a conductivity signal;

a temperature detecting device; and a controller configured to receive at least a temperature signal from the temperature detecting device and a conductivity signal from the fluid conductivity measuring portion, wherein, the disposable portion is connected to convey the mixed product, the temperature detecting device is in contact with the disposable portion and adapted to measure a temperature of the mixed product and to output the temperature signal, the controller is configured to control a relative flow of water and a concentrate responsively to both of said temperature and conductivity signals, and the temperature detecting device includes a first temperature sensor attached to a flat member that is adapted to be placed against a wall of the disposable portion, a second temperature sensor separated from the first temperature sensor by a thermal insulator, a temperature regulating device in thermal contact with the second temperature sensor and a temperature controller configured to receive first and second temperature indication signals, respectively, from the first and second temperature sensors and to regulate said temperature regulating device responsively to the first and second temperature indication signals.

2. The system of claim 1, wherein the controller is configured for feedback control of a concentration of said mixed product.

3. The system of claim 1, wherein the controller is configured to calculate, or look up in a data store, a parameter dependent on a concentration of the mixed product and to employ it as a feedback control signal to regulate concentration of said mixed product.

4. The system of claim 1, wherein
the thermal insulator is an insulating air gap.

5. The system of claim 1, wherein
the thermal insulator includes multiple layers of materials.

6. The system of claim 5, wherein
the thermal insulator includes layers of high conductivity materials to promote transfer of heat in specific directions.

* * * * *